(12) United States Patent
Martin et al.

(10) Patent No.: US 11,390,840 B2
(45) Date of Patent: Jul. 19, 2022

(54) SYSTEMS AND METHODS INCLUDING POROUS MEMBRANE FOR LOW-VOLTAGE CONTINUOUS CELL ELECTROPORATION

(71) Applicant: University of Florida Research Foundation, Inc., Gainesville, FL (US)

(72) Inventors: Charles R. Martin, Gainesville, FL (US); Juliette Experton, Gainesville, FL (US); Aaron G. Wilson, Pace, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 270 days.

(21) Appl. No.: 16/337,677

(22) PCT Filed: Sep. 29, 2017

(86) PCT No.: PCT/US2017/054273
§ 371 (c)(1),
(2) Date: Mar. 28, 2019

(87) PCT Pub. No.: WO2018/064463
PCT Pub. Date: Apr. 5, 2018

(65) Prior Publication Data
US 2020/0032190 A1    Jan. 30, 2020

Related U.S. Application Data

(60) Provisional application No. 62/402,472, filed on Sep. 30, 2016.

(51) Int. Cl.
*C12M 3/00* (2006.01)
*C12N 15/00* (2006.01)
(Continued)

(52) U.S. Cl.
CPC ............ *C12M 35/02* (2013.01); *C12M 29/04* (2013.01); *C12N 13/00* (2013.01); *C12N 15/87* (2013.01)

(58) Field of Classification Search
CPC ......... C12M 35/02; C12N 13/00; C12N 15/87
See application file for complete search history.

(56) References Cited

U.S. PATENT DOCUMENTS 5,098,843 A * 3/1992 Calvin .................. C12N 15/87
                                                              435/173.6
5,283,194 A * 2/1994 Schmukler ............ C12M 35/02
                                                              435/173.6
(Continued)

OTHER PUBLICATIONS

Adamo, Andrea, et al. "Flow-through comb electroporation device for delivery of macromolecules." Analytical chemistry 85.3 (2013): 1637-1641.
(Continued)

*Primary Examiner* — Nathan A Bowers
(74) *Attorney, Agent, or Firm* — Thomas | Horstemeyer, LLP

(57) ABSTRACT

Described herein are systems and methods of flow-through electroporation can comprise a chamber with a first and a second portion, wherein the first portion is configured to receive cells and the second portion is in fluid communication with the first portion and is configured to receive cells from the first portion; an electrode can be present in the first portion, second portion, or both; a porous membrane can separate the first and second portions, the porous membrane can have one or more pores, and the pores can have one or more interior surfaces configured to allow cells from the first portion to pass through to the second portion; an electric generating device in electrical communication with one or more electrodes, the membrane, or the one or more electrodes and the membrane, wherein the electric generating (Continued)

device is configured to deliver constant voltage or one or more electric pulses to the system.

19 Claims, 23 Drawing Sheets

(51) Int. Cl.
    *C12N 13/00*     (2006.01)
    *C12M 1/42*     (2006.01)
    *C12M 1/00*     (2006.01)
    *C12N 15/87*     (2006.01)

(56) References Cited

U.S. PATENT DOCUMENTS

| | | | |
|---|---|---|---|
| 7,197,359 B1* | 3/2007 | Tokudome | A61K 9/0009 424/448 |
| 7,358,077 B2 | 4/2008 | Zimmermann et al. | |
| 7,456,012 B2 | 11/2008 | Ryttsen et al. | |
| 2002/0063067 A1* | 5/2002 | Bech | B01L 3/0262 205/775 |
| 2003/0107386 A1* | 6/2003 | Dodgson | G01N 33/48728 324/699 |
| 2003/0148524 A1 | 8/2003 | Zimmermann et al. | |
| 2004/0029240 A1 | 2/2004 | Acker | |
| 2005/0170510 A1 | 8/2005 | Huang et al. | |
| 2005/0282200 A1* | 12/2005 | Dzekunov | C12M 41/00 435/6.12 |
| 2006/0281168 A1* | 12/2006 | Futami | C12M 35/02 435/285.2 |
| 2007/0066959 A1 | 3/2007 | Seward | |
| 2009/0004717 A1 | 1/2009 | Jaroszeski et al. | |
| 2009/0269317 A1 | 10/2009 | Davalos | |
| 2012/0276635 A1 | 11/2012 | Lu et al. | |
| 2013/0066296 A1* | 3/2013 | Broderick | A61N 1/0502 604/501 |
| 2014/0106429 A1 | 4/2014 | Sridharan et al. | |

OTHER PUBLICATIONS

Agarwal, Aparna, et al. "Control of the release of freely diffusing molecules in single-cell electroporation." Analytical chemistry 81.19 (2009): 8001-8008.

Boukany, Pouyan E., et al. "Nanochannel electroporation delivers precise amounts of biomolecules into living cells." Nature nanotechnology 6.11 (2011): 747-754.

Canatella, Paul J., et al. "Quantitative study of electroporation-mediated molecular uptake and cell viability." Biophysical journal 80.2 (2001): 755-764.

Chang, Lingqian, et al. "Magnetic tweezers-based 3D microchannel electroporation for high-throughput gene transfection in living cells." Small 11.15 (2015): 1818-1828.

Chang, Lingqian, et al. "3D nanochannel electroporation for high-throughput cell transfection with high uniformity and dosage control." Nanoscale 8.1 (2016): 243-252.

Choi, Seong-O., et al. "Intracellular protein delivery and gene transfection by electroporation using a microneedle electrode array." Small 8.7 (2012): 1081-1091.

Deng, Jingdong, et al. "The effects of intense submicrosecond electrical pulses on cells." Biophysical journal 84.4 (2003): 2709-2714.

Dower, William J.; et al. "High efficiency transformation of E. coli by high voltage electroporation." Nucleic acids research 16.13 (1988): 6127-6145.

Fei, Zhengzheng, et al. "Micronozzle array enhanced sandwich electroporation of embryonic stem cells." Analytical chemistry 82.1 (2010): 353-358.

Fox, M. B., et al. "Electroporation of cells in microfluidic devices: a review." Analytical and bioanalytical chemistry 385.3 (2006): 474-485.

Fujii, Shunjiro, et al. "Efficient field emission from an individual aligned carbon nanotube bundle enhanced by edge effect." Applied Physics Letters 90.15 (2007): 153108.

Gao, Peng, and Charles R. Martin. "Voltage charging enhances ionic conductivity in gold nanotube membranes." ACS nano 8.8 (2014): 8266-8272.

Gao, Keliang, et al. "Design of a Microchannel-Nanochannel-Microchannel Array Based Nanoelectroporation System for Precise Gene Transfection." Small 10.5 (2014): 1015-1023.

Garcia, Paulo A., et al. "Microfluidic screening of electric fields for electroporation." Scientific reports 6.1 (2016): 1-11.

Gehl, J. "Electroporation: theory and methods, perspectives for drug delivery, gene therapy and research." Acta Physiologica Scandinavica 177.4 (2003): 437-447.

Geng, Tao; et al. "Microfluidic electroporation for cellular analysis and delivery." Lab on a Chip 13.19 (2013): 3803-3821.

Geng, Tao, et al. "Transfection of cells using flow-through electroporation based on constant voltage." nature protocols 6.8 (2011): 1192-1208.

Hosic, Sanjin; et al. "Microfluidic sample preparation for single cell analysis." Analytical chemistry 88.1 (2016): 354-380.

Huang, Yong; et al. "Microfabricated electroporation chip for single cell membrane permeabilization." Sensors and Actuators A: Physical 89.3 (2001): 242-249.

Jiang, Zhijun; et al. "Charge regulation in nanopore ionic field-effect transistors." Physical Review E 83.3 (2011): 031203.

Kang, Mun-Sik; et al.. "Investigations of potential-dependent fluxes of ionic permeates in gold nanotubule membranes prepared via the template method." Langmuir 17.9 (2001): 2753-2759.

Kim, Soo Hyeon, et al. "Electroactive microwell arrays for highly efficient single-cell trapping and analysis." Small 7.22 (2011): 3239-3247.

Kim, Sang Kyung, et al. "Continuous low-voltage dc electroporation on a microfluidic chip with polyelectrolytic salt bridges." Analytical chemistry 79.20 (2007): 7761-7766.

Kotnik, Tadej, et al. "Electroporation-based applications in biotechnology." Trends in biotechnology 33.8 (2015): 480-488.

Kovarik, Michelle L., et al. "Micro total analysis systems for cell biology and biochemical assays." Analytical chemistry 84.2 (2012): 516-540.

Lee, Won Gu; et al. "Microscale electroporation: challenges and perspectives for clinical applications." Integrative Biology 1.3 (2009): 242-251.

Lee, Sang Bok; et al. "Electromodulated molecular transport in gold-nanotube membranes." Journal of the American Chemical Society 124.40 (2002): 11850-11851.

Liu, Chong, et al. "Conducting nanosponge electroporation for affordable and high-efficiency disinfection of bacteria and viruses in water." Nano letters 13.9 (2013): 4288-4293.

Lord, Samuel J; et al. "Single-molecule spectroscopy and imaging of biomolecules in living cells." Analytical chemistry 82.6 (2010): 2192-2203.

Luo, Dan; et al. "Synthetic DNA delivery systems." Nature biotechnology 18.1 (2000): 33-37.

Martin, Charles R., et al. "Investigations of the transport properties of gold nanotubule membranes." The Journal of Physical Chemistry B 105.10 (2001): 1925-1934.

Martin, Charles R. "Nanomaterials: a membrane-based synthetic approach." Science 266.5193 (1994): 1961-1966.

Menon, Vinod P; et al. "Fabrication and evaluation of nanoelectrode ensembles." Analytical Chemistry 67.13 (1995): 1920-1928.

Movahed, Saeid; et al. "Microfluidics cell electroporation." Microfluidics and Nanofluidics 10.4 (2011): 703-734.

Myers, John A; et al. "Improving accuracy of cell and chromophore concentration measurements using optical density." BMC biophysics 6.1 (2013): 1-16.

Nelson, Edward M., et al. "Using a nanopore for single molecule detection and single cell transfection." Analyst 137.13 (2012): 3020-3027.

Netzel, Thomas L., et al. "Base-content dependence of emission enhancements, quantum yields, and lifetimes for cyanine dyes bound to double-strand DNA: photophysical properties of mono-

(56) References Cited

OTHER PUBLICATIONS meric and bichromomphoric DNA stains." The Journal of Physical Chemistry 99.51 (1995): 17936-17947.
Nishizawa, Matsuhiko; et al. "Metal nanotubule membranes with electrochemically switchable ion-transport selectivity." Science 268. 5211 (1995): 700-702.
Olofsson, Jessica, et al. "Single-cell electroporation." Current opinion in biotechnology 14.1 (2003): 29-34.
Pakhomov, Andrei G., et al. "Multiple nanosecond electric pulses increase the number but not the size of long-lived nanopores in the cell membrane." Biochimica et Biophysica Acta (BBA)-Biomembranes 1848.4 (2015): 958-966.
Rizzello, Loris, et al. "Impact of nanoscale topography on genomics and proteomics of adherent bacteria." Acs Nano 5.3 (2011): 1865-1876.
Schoenbach, Karl H., et al. "The effect of pulsed electric fields on biological cells: Experiments and applications." IEEE transactions on plasma science 25.2 (1997): 284-292.
Sezonov, Guennadi; et al. "*Escherichia coli* physiology in Luria-Bertani broth." Journal of bacteriology 189.23 (2007): 8746-8749.
Stampfli, R. "Reversible electrical breakdown of the excitable membrane of a Ranvier node." An Acad Brasil Ciens 30.1 (1958): 57-61.
Vernier, P. Thomas; et al. "Nanoelectropulse-driven membrane perturbation and small molecule permeabilization." BMC cell biology 7.1 (2006): 1-16.
Voldman, Joel. "Electrical forces for microscale cell manipulation." Annu. Rev. Biomed. Eng. 8 (2006): 425-454.
Wang, Shengnian, and L. James Lee. "Micro-/nanofluidics based cell electroporation." Biomicrofluidics 7.1 (2013): 011301.
Weaver, James C; et al. "Theory of electroporation: a review." Bioelectrochemistry and bioenergetics 41.2 (1996): 135-160.
White, Henry S; et al. "Ion current rectification at nanopores in glass membranes." Langmuir 24.5 (2008): 2212-2218.
International Search Report and Written Opinion for PCT/US2017/054273 dated Dec. 14, 2017.
Xie, Xi, et al. "Nanostraw-electroporation system for highly efficient intracellular delivery and transfection." ACS nano 7.5 (2013): 4351-4358.
Yi, Changqing, et al. "Microfluidics technology for manipulation and analysis of biological cells." Analytica chimica acta 560.1-2 (2006): 1-23.
Zhao, Deyao, et al. "A flow-through cell electroporation device for rapidly and efficiently transfecting massive amounts of cells in vitro and ex vivo." Scientific reports 6.1 (2016): 1-9.
Vorobiev, Eugene; et al. "Electrotechnologies for extraction from food plants and biomaterials." vol. 5996. New York: Springer, 2008; pp. 1-37.
Allen, J. Bard; et al. "Electrochemical methods fundamentals and applications." John Wiley & Sons, 2001; p. 864. \*\*Separated into 8 separate Files\*\*.

\* cited by examiner

```
┌─────────────────────────────┐
│  Prepare suspension of cells │
└─────────────────────────────┘
```
```
┌──────────────────────────────────────────────────┐
│ Pass suspension of cells through one or more pores│
│         of a porous membrane while a              │
│ continuous voltage or one or more electric pulses are│
│         applied to or across the membrane         │
└──────────────────────────────────────────────────┘
```
```
┌──────────────────────────────────────┐
│   Collect cells with a collection device │
└──────────────────────────────────────┘
```

FIG. 1

| Pore Diameter [μm] | Pore Density [$cm^{-2}$] |
|---|---|
| 3 | $2 \times 10^6$ |
| 5 | $5 \times 10^5$ |
| 10 | $1 \times 10^5$ |
| 20 | $4 \times 10^4$ |

FIG. 23

SYSTEMS AND METHODS INCLUDING POROUS MEMBRANE FOR LOW-VOLTAGE CONTINUOUS CELL ELECTROPORATION

CROSS-REFERENCE TO RELATED APPLICATION

This application is the 35 U.S.C. 371 national stage application of PCT Application No. PCT/US2017/054273, filed Sep. 29, 2017, where the PCT claims priority to U.S. provisional application entitled "SYSTEMS AND METHODS INCLUDING POROUS MEMBRANE FOR LOW-VOLTAGE CONTINUOUS CELL ELECTROPORATION" having Ser. No. 62/402,472 filed on Sep. 30, 2016, both of which are entirely incorporated herein by reference.

BACKGROUND

Electroporation is a technique that uses electric fields to disrupt cell membranes, and can be irreversible or reversible. Irreversible electroporation creates permanent holes in cellular membranes and is lethal to cells. On the other hand, reversible electroporation is transient and creates temporary nano-scale holes in cellular membranes that allows for the passage of materials from the outside of the cell to the inside and vice versa. Reversible electroporation can be used to deliver membrane-impermeable exogenous agents, such as nucleic acids, to a cell. Most commonly-used devices and methods for reversible electroporation currently employ cuvettes with electrodes separated by millimeter-scale distances. This large distance between electrodes is problematic because a large voltage is needed, which provides high cell mortality as a result of apoptosis due to irreversible intracellular phenomena. Additionally, the large distance between the electrodes leads to an unstable and non-uniform electric field.

Other approaches, such as the use of nanoporous filter membranes and silicon wafers, have been used to address the above issues. These approaches are also sub-optimal because of low cell throughput, and they are relatively complicated to implement in molecular biology. Accordingly, there is a need to address the aforementioned deficiencies and inadequacies.

SUMMARY

Described herein are flow-through electroporation systems. Flow through electroporation systems as described herein can comprise a chamber with a first and a second portion, wherein the first portion is configured to receive cells and the second portion is in fluid communication with the first portion and is configured to receive cells from the first portion; an electrode can be present in the first portion, second portion, or both; a porous membrane can separate the first and second portions, the porous membrane can have one or more pores, and the pores can have one or more interior surfaces configured to allow cells from the first portion to pass through to the second portion; systems as described herein can have an electric generating device in electrical communication with one or more electrodes, the membrane, or the one or more electrodes and the membrane, wherein the electric generating device is configured to deliver constant voltage or one or more electric pulses to the system.

The first portion of systems as described herein can further be configured to receive air. The second portion or systems as described herein can further comprise a stirring device to stir a solution containing cells that have passed through the membrane. Systems as described herein can further comprising a pump in fluid communication with the first or second portion of the chamber, individually or in combination. The second portion of the chamber of systems described herein can be configured to release cells from the system.

Porous membranes of systems as described herein can have a thickness of about 100 nm to 10 cm. A pore or pores of the porous membrane can have an average diameter of about 10 nm to about 5 mm and a length of about 100 nm to about 10 cm. Pore density of the porous membrane can be about 1 pore/m$^2$ to about $10^{15}$ pores/cm$^2$.

In certain aspects, electric pulses delivered to the system and/or membrane comprise a −4 V volt DC pulse with a 30 ms duration and a period of 250 ms. In certain aspects, electric pulses delivered to the system and/or membrane are not a −4 V volt DC pulse with a 30 ms duration and a period of 250 ms.

Systems as described herein can comprise a cooling device to lower the temperature of the second portion. Systems as described herein can comprise a cooling device to lower the temperature of the second portion below ambient (room) temperature. Systems as described herein can comprise a warming device to warm or heat the temperature of the second portion. Systems as described herein can comprise a warming device to warm or heat the temperature of the second portion above (room) ambient temperature.

In certain aspects, the porous membrane of systems described herein is coated with a conductive material on one or more sides. In certain aspects, one or more pores of the porous membrane are coated with a conductive material on one or more interior surfaces.

The conductive material which can coat the membrane, pores, or both cab be a metal selected from the group consisting of gold, silver, platinum, nickel, aluminum, tin, copper, molybdenum, zinc, tungsten, carbon, iron, palladium, titanium, lead, mercury, lithium, brass, metal oxides, manganese, magnesium and combinations thereof.

Porous membranes as described herein can comprise gold, silver, platinum, nickel, aluminum, tin, copper, molybdenum, zinc, tungsten, carbon, iron, palladium, titanium, lead, mercury, lithium, brass, manganese, magnesium, metal oxides or combinations thereof.

Porous membranes as described herein can further comprise polycarbonate, polyethylene terephthalate, myca, aluminum, aluminum oxide, nylon, polytetrafluoroethylene, silicon, cellulose, polypropylene, polyvinylidene fluoride, silver, polyethersulfone, or combinations thereof.

Also described herein are electroporation methods. Without intending to be limiting, electroporation methods as described herein can comprise the steps of: preparing a suspension of cells, the suspension of cells having a temperature; applying a continuous voltage or one or more electric pulses to or across a porous membrane to create an electric field gradient, the porous membrane having one or more pores, passing the suspension of cells through the one or more pores of the porous membrane while a continuous voltage or one or more electric pulses are applied to or across the porous membrane to increase the permeability of the cell membrane, cell wall, or both; and collecting the cells that pass through the one or more pores of the porous membrane with a collection device configured to receive cells that pass through the membrane. One of skill in the art would recognize that steps of methods as described herein may be interchangeable and can be performed in orders that are different that as described.

Methods as described herein can further comprise stirring the cells in the collection device. Methods as described herein can further comprise cooling the collection chamber before or after cells pass through the membrane. Methods as described herein can further comprised cooling the collection chamber before or after cells pass through the membrane below ambient (room) temperature.

Methods as described herein can further comprise warming or heating the collection chamber before or after cells pass through the membrane. Methods as described herein can further comprised warming or heating the collection chamber before or after cells pass through the membrane above ambient (room) temperature.

Porous membranes used in methods as described herein can have a thickness of about 100 nm to about 10 cm. Porous membranes used in methods as described herein can have one or more pores have an average diameter of about 10 nm to about 5 mm, a length of about 100 nm to about 10 cm, and/or a density of about 1 pore/m$^2$ to about $10^{15}$ pores/cm$^2$.

Methods as described herein can utilize one or more −4V pulses with a 30 ms duration and a period between pulses of 250 ms. In certain aspects, methods as described herein do not use −4V pulses with a 30 ms duration and a period between pulses of 250 ms.

Without intending to be limiting, the suspension of cells utilized in methods as described herein can comprises *E. coli* and an exogenous agent. Although *E.coli* is described, other prokaryotic and eukaryotic cell types (such as those described below) can be used in methods as described herein. The suspension of cells utilized in methods as described herein can comprises *E. coli* and an exogenous agent and the one or more electric pulses comprise −4V pulses with a 30 ms duration and a period between pulses of 250 ms.

Exogenous agents as described herein can be one or more nucleic acids. Exogenous agents as described herein can be vectors for the expression of one or more coding RNA coding sequences, for example a plasmid vector configured for the expression of green fluorescent protein (GFP) in a cell which uptakes the vector according to methods as described herein, in the cytoplasm, nucleus, or both.

The electric field gradient in methods as described herein can be about 1 kV/cm to about 200 kV/cm.

The porous membrane utilized in methods as described herein can be coated on one or more sides with a conductive material. The porous membrane utilized in methods as described herein can contain one or more pores, the pores with one or more interior surfaces coated with a conductive material. The conductive material is a metal selected from the group consisting of gold, silver, platinum, nickel, aluminum, tin, copper, molybdenum, zinc, tungsten, carbon, iron, palladium, titanium, lead, mercury, lithium, brass, manganese, magnesium, metal oxides and combinations thereof.

Methods as described herein can also comprise washing the membrane with a wash volume of media after passing the suspension of cells through one or more pores of the porous membrane; and passing the wash volume of media through one or more pores of the porous membrane while a continuous voltage or one or more electric pulses are applied to or across the membrane.

Porous membranes as described in systems and methods herein can comprise gold, silver, platinum, nickel, aluminum, tin, copper, molybdenum, zinc, tungsten, carbon, iron, palladium, titanium, lead, mercury, lithium, brass, metal manganese, magnesium, oxides or combinations thereof.

Porous membranes as described in systems and methods herein can further comprise polycarbonate, polyethylene terephthalate, myca, aluminum, aluminum oxide, nylon, polytetrafluoroethylene, silicon, cellulose, polypropylene, polyvinylidene fluoride, silver, polyethersulfone, or combinations thereof.

In certain embodiments, described herein are flow-through electroporation systems comprising: a chamber with a first and a second portion, the first portion being configured to receive cells, the second portion being in fluid communication with the first
portion and configured to receive cells from the first portion, and electrode is present in second portion; a porous membrane can separate the first and second portions, the membrane having one or more pores with a pore density of about 1 pore/m$^2$ to about $10^{15}$ pores/cm$^2$, and the one or more pores have one or more interior surfaces and are configured to allow cells from the first portion to pass through to the second portion; and
an electric generating device in electrical communication with one or more electrodes, the membrane, or the one or more electrodes and the membrane, wherein the electric generating device is configured to deliver constant voltage or one or more electric pulses to the system; and a cooling device to lower the temperature of the second portion.

The first portion (which also can be referred to as a first chamber or feed chamber) can be further configured to receive a volume of cells less than 1 mL. The second portion (which can also be referred to as a second chamber or receiving chamber) further comprises a stirring device. In embodiments, systems and methods as described herein can contain or utilize a pump in fluid communication with the first or second portion of the chamber, individually or in combination that can help the passage of fluid containing cells from the first portion through the membrane to the second portion, out of the system, or both. The second portion of the chamber of systems as described herein can be further configured to release cells from the system.

Porous membranes of systems and methods as described herein can have a thickness of about 100 nm to 10 cm. One or more pores of porous membranes as described herein can have an average diameter of about 10nm to about 5 mm, and/or a length of about 100 nm to about 10 cm.

Porous membranes as described herein can be coated with a conductive material on one or more sides. One or more pores of membranes as described herein can be coated on one or more interior surfaces. The conductive material is a metal selected from the group consisting of gold, silver, platinum, nickel, aluminum, tin, copper, molybdenum, zinc, tungsten, carbon, iron, palladium, titanium, lead, mercury, lithium, brass, manganese, magnesium, metal oxides and combinations thereof.

Porous membranes as described herein can comprise gold, silver, platinum, nickel, aluminum, tin, copper, molybdenum, zinc, tungsten, carbon, iron, palladium, titanium, lead, mercury, lithium, brass, metal oxides and combinations thereof.

Porous membranes as described herein can further comprise polycarbonate, polyethylene terephthalate, myca, aluminum, aluminum oxide, nylon, polytetrafluoroethylene, silicon, cellulose, polypropylene, polyvinylidene fluoride, silver, polyethersulfone, or combinations thereof. In certain embodiments, methods as described herein can comprise the steps of: preparing a suspension of cells, the suspension of cells having a first temperature; applying a continuous voltage or one or more electric pulses to or across a porous membrane to create an electric field gradient, the porous membrane having one or more pores with a pore density 1 pore/m$^2$ to about 10$^{15}$ pores/cm$^2$, passing the suspension of cells through the one or more pores of the porous membrane while a continuous voltage or one or more electric pulses are applied to or across the porous membrane to increase the permeability of the cell membrane, cell wall, or both; collecting the cells that pass through the one or more pores of the porous membrane with a collection device configured to receive cells that pass through the membrane; and cooling the cells in the collection device to a second temperature that is lower than the first temperature.

Methods as described herein can also comprise stirring the cells in the collection device.

Porous membranes used in embodiments of methods as described herein can have a thickness of about 100 nm to about 10 cm and can contain one or more pores with an average diameter of about 10 nm to about 5 mm, and a length of about 100 nm to about 10 cm, and/or pore densities with ranges as described herein.

In certain aspects, one or more electric pulses of embodiments of methods as described herein can be −4mV pulses with a 30 ms duration and a period between pulses of 250 ms. In certain aspects, one or more electric pulses of embodiments of methods as described herein are not −4V pulses with a 30 ms duration and a period between pulses of 250 ms.

The suspension of cells utilized in methods as described herein can comprise E. coli and an exogenous agent and the one or more electric pulses comprise −4V pulses with a 30 ms duration and a period between pulses of 250 ms. The suspension of cells utilized in methods as described herein can comprise E. coli and an exogenous agent and the one or more electric pulses are not −4V pulses with a 30 ms duration and a period between pulses of 250 ms. As previously described, methods as described herein are applicable to other prokaryotic and eukaryotic cell types than just E. coli.

Exogenous agents as described herein can be one or more nucleic acids. The electric field gradient of embodiments and methods as described herein can be about 1 kV/cm to about 200 kV/cm.

Membranes as described herein can be coated on one or more sides with a conductive material. One or more pores of membranes as described herein can have one or more interior surfaces coated with a conductive material. The conductive material can be a metal selected from the group consisting of gold, silver, platinum, nickel, aluminum, tin, copper, molybdenum, zinc, tungsten, carbon, iron, palladium, titanium, lead, mercury, lithium, brass, manganese, magnesium metal oxides and combinations thereof.

Embodiments of methods as described herein can also comprise washing the membrane with a wash volume of media after passing the suspension of cells through one or more pores of the porous membrane; and passing the wash volume of media through one or more pores of the porous membrane while a continuous voltage or one or more electric pulses are applied to or across the membrane.

Porous membranes of embodiments of systems and methods as described herein can contain gold, silver, platinum, nickel, aluminum, tin, copper, molybdenum, zinc, tungsten, carbon, iron, palladium, titanium, lead, mercury, lithium, brass, metal oxides and combinations thereof.

Porous membranes of systems and methods as described herein can also contain polycarbonate, polyethylene terephthalate, myca, aluminum, aluminum oxide, nylon, polytetrafluoroethylene, silicon, cellulose, polypropylene, polyvinylidene fluoride, silver, polyethersulfone, or combinations thereof.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

FIG. 1 depicts an embodiment of a method according to the present disclosure.

FIG. 23 shows embodiments of average pore diameters and pore densities according to the present disclosure.

DETAILED DESCRIPTION

Figure 2:
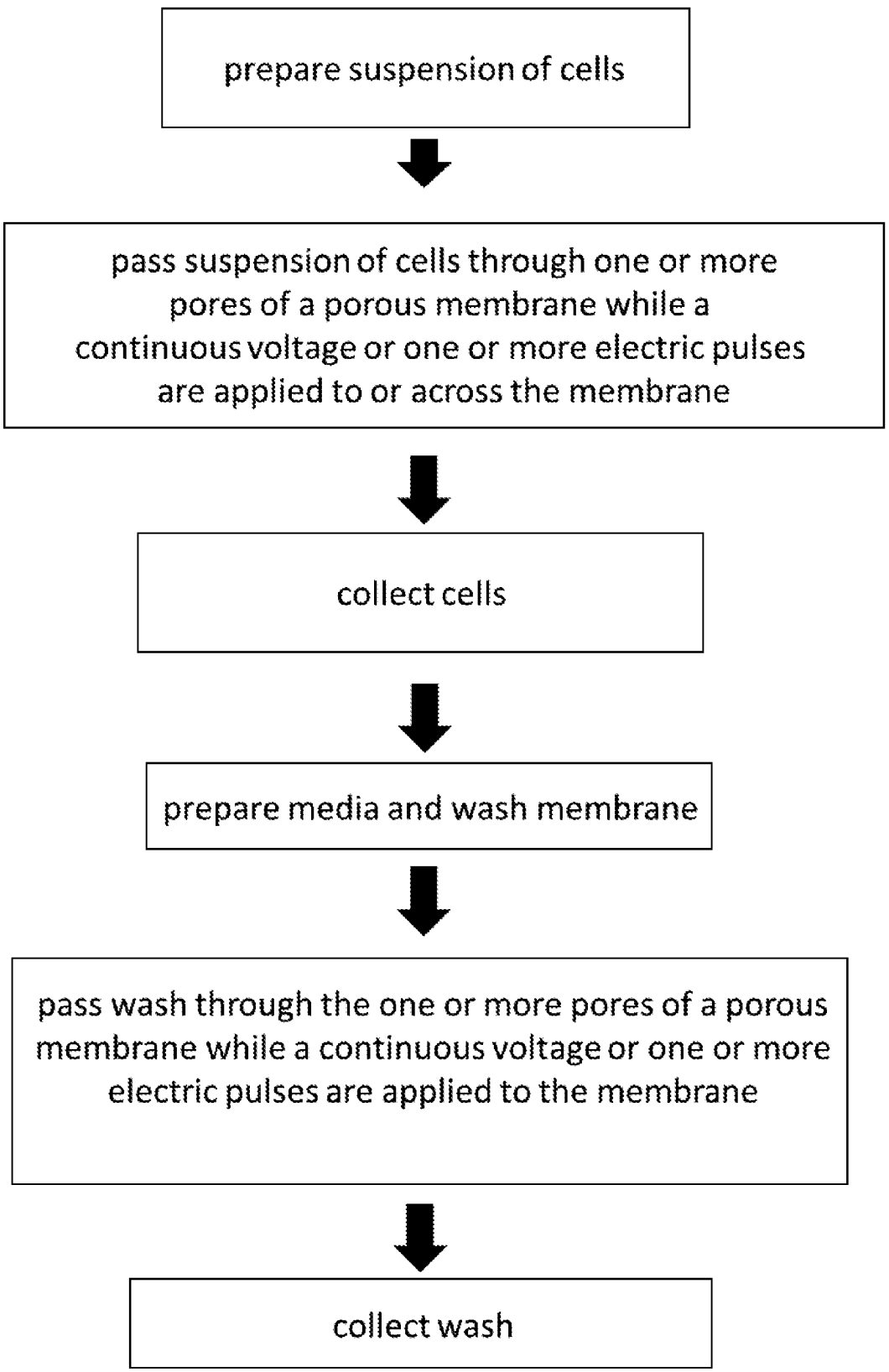
FIG. 2 depicts an embodiment of a method according to the present disclosure.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, material science, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmosphere. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Discussion

Embodiments of the present disclosure provide for systems and methods relating to continuous cell electroporation and porous membranes. Discussed herein are embodiments of devices for continuous cell electroporation that utilize porous membranes in addition to embodiments of methods of continuous cell electroporation using embodiments of such devices.

Systems and methods as described herein can include porous membranes. Porous membranes (also referred to herein as "membranes") can be used for efficient cell electroporation, providing high electric fields at low voltages and minimizing detrimental effects of conventional electroporation due to processes such as heating, pH change, and metal ion dissolution.

A porous membrane as described herein can have a top, a bottom, and one or more sides. A porous membrane can have a surface area and a thickness, and the size of the surface area and thickness of the membrane can be tailored to the desired application throughput. The surface area of a porous membrane can be on a millimeter scale, centimeter scale, meter scale, or other scale, with larger surface areas being suitable for increased throughput.

A porous membrane as described herein can be constructed from an electrically non-conductive material or an electrically conductive material. In certain embodiments, a porous membrane can be polycarbonate, polyethylene terephthalate, myca, aluminum, aluminum oxide, nylon, polytetrafluoroethylene, silicon, cellulose, polypropylene, polyvinylidene fluoride, silver, polyethersulfone, or combinations thereof. In an embodiment, a membrane can be a polycarbonate membrane and have a thickness of about 100 nm to about 10 cm. In an embodiment, a membrane can be a polycarbonate membrane and have a thickness of about 10 μm. Porous membranes as described herein can be constructed from a conductive material. In embodiments of the present disclosure, the conductive material can be gold, silver, platinum, nickel, aluminum, tin, copper, molybdenum, zinc, tungsten, carbon, iron, palladium, titanium, lead, mercury, lithium, brass, manganese, magnesium, metal oxides and combinations thereof.

Porous membranes as described herein can be coated with a conductive material to form a conductive membrane. Coated as used herein is not intended to be limiting and can mean plated, deposited, laminated, painted, stained, or otherwise applied. Coating as used herein is not intended to limit the manufacturing process by which a layer of conductive material is applied to a surface, and can mean plated, electroplated, deposited (i.e., chemical vapor deposition or physical vapor deposition, for example), painted, stained, sputtered, or other suitable manufacturing technique to place a layer of conductive material on a surface. The coating can be a continuous coating that coats at least one of the top, sides, and bottom of the membrane. In an embodiment, the continuous coating can have a thickness of about 1 nm to 10 cm. In certain embodiments, the conductive material can be a material that has a conductivity equal to or greater than about $10^5$ S/m. The conductive material can be a metal. In an embodiment, the conductive material can be gold, silver, platinum, nickel, aluminum, tin, copper, molybdenum, zinc, tungsten, carbon, iron, palladium, titanium, lead, mercury, lithium, brass, manganese, magnesium, metal oxides and combinations thereof. In an embodiment, the conductive material is gold (Au). In certain embodiments, the conductive material is not gold (Au).

The conductive material can be removed from one or more sides of a membrane. In embodiment, the conductive material is removed from the top of the membrane. The conductive material can be removed chemically, such as with a solvent, or mechanically, such as by scrubbing. Chemical and mechanical means can be combined to remove the conductive material from one or more sides of the conductive porous membrane.

In an embodiment, gold is the conductive material, and gold is removed from the top of membrane with scrubbing using an abrasive material so that only the bottom and insides of the pores (or tubes) are coated with gold. The conductive surface of a conductive porous membrane can be part of an electric circuit, and one or more electric pulses can be delivered to or across a conductive surface of a membrane.

In embodiments, porous membranes can contain pores and can be porous conductive membranes (also referred to herein as "membranes", "conductive porous membranes", "conductive membranes", "microporous membranes", "microtube membranes"). Pores (also herein referred to as "pores", "tubes", or "microtubes") can have an average diameter and a length. An average pore diameter can be about 10 nm to about 200 μm, about 20 nm to about 190 μm, about 30 nm to about 180 μm, about 40 nm to about 170 μm, about 50 nm to about 160 μm, about 60 nm to about 150 μm, about 70 nm to about 140 μm, about 80 nm to about 130 μm, about 90 nm to about 120 μm, about 100 nm to about 110 μm, about 200 nm to about 100 μm, about 300 nm to about 90 μm, about 400 nm to about 80 μm, about 500 nm to about 70 μm, about 600 nm to about 60 μm, about 700 nm to about 50 μm, about 800 nm to about 40 μm, about 900 nm to about 30 μm, about 1 μm to about 20 μm, about 1 μm to about 4 μm.

In an embodiment, the average pore diameter can be about 5 mm or less. Average pore diameter can be about 1 mm to about 5 mm; about 1 mm to about 4 mm; about 1 mm to about 3 mm; or about 1 mm to about 2 mm. Average pore diameter can be about 1 μm to about 1 mm; about 10 pm to about 900 μm; about 100 μm to about 800 μm; about 200 μm to about 700 μm; about 300 μm to about 600 μm; about 400 μm to about 500 μm. An average pore diameter can be about 10 nm to about 1 μm, about 100 nm to about 900 μm; about 200 nm to about 800 μm; about 300 nm to about 700 μm; about 400 nm to about 600 μm; or about 500 nm. An average pore diameter can be about 3 μm to about 20 μm, about 4 μm to about 19 μm, about 5 μm to about 18 μm, about 6 μm to about 17 μm, about 7 μm to about 16 μm, about 8 μm to about 15 μm, about 9 μm to about 14 μm, about 10 μm to about 13 μm, or about 11 μm to about 12 μm. In certain embodiments, pore diameter is not 0.1 μm to 20 μm.

One skilled in the art would appreciate that pore diameter is dependent on the cell type to be electroporated, and in general smaller pores are suitable for electroporation of smaller cells, and larger pores suitable for electroporation of larger cells. Pores as described herein can take on many geometries (cylindrical, conical, rectangular, etc.) and can have one or more interior surfaces. The one or more interior surfaces of a membrane can be coated with a conductive material or can lack a coating of conductive material. In certain embodiments, the pores of the membrane lack coating of a conductive material throughout the pore opening and length.

Average diameter of pores can be application-dependent and depend on the size of the cells to be electroporated and scaled accordingly, and larger cells can utilize larger pores. In an embodiment, average pore diameter is about 5 μm. In an embodiment, average pore diameter is about 5 pm and suitable for electroporating E. coli. Pores can be filled with an electrolyte-containing solution.

Pore length can be about the same as the thickness of the membrane (or the dimension spanning the top to the bottom), and a pore can span the thickness of the membrane. Pore length can span from the top of a membrane to the bottom of a membrane. Pore length can be the smallest dimension of a membrane. Average pore length can be about 100 nm to about 10 cm, and the average pore length can be thickness of the membrane. In an embodiment, average pore length is about 10 µm. In an embodiment, average pore diameter is about 5 µm and average pore length is about 10 µm. Average pore length can be about 1 cm or less.

Porous membranes can also have a density of pores throughout the membrane. A membrane of the present disclosure can have a pore density of about one pore per membrane to about $10^{15}$ pores/cm$^2$ per membrane. A membrane of the present disclosure can have a pore density of about $10^1$ pores/cm$^2$ per membrane to about $10^{15}$ pores/cm$^2$ per membrane. A membrane of the present disclosure can have a pore density of about $10^2$ pores/cm$^2$ per membrane to about $10^{14}$ pores/cm$^2$ per membrane. A membrane of the present disclosure can have a pore density of about $10^3$ pores/cm$^2$ per membrane to about $10^{13}$ pores/cm$^2$ per membrane. A membrane of the present disclosure can have a pore density of about $10^4$ pores/cm$^2$ per membrane to about $10^{12}$ pores/cm$^2$ per membrane. A membrane of the present disclosure can have a pore density of about $10^5$ pores/cm$^2$ per membrane to about $10^{11}$ pores/cm$^2$ per membrane. A membrane of the present disclosure can have a pore density of about $10^6$ pores/cm$^2$ per membrane to about $10^{10}$ pores/cm$^2$ per membrane. A membrane of the present disclosure can have a pore density of about $10^7$ pores/cm$^2$ per membrane to about $10^9$ pores/cm$^2$ per membrane. A membrane of the present disclosure can have a pore density of about $10^8$ pores/cm$^2$ per membrane.

Porous membranes and systems and methods as described herein can be configured to provide an electric field to a cell, the electric field strength having a magnitude of about 1 V/cm to about 200 kV/cm, about 100 V/cm to about 1 kV/cm, about 1 to about 5 kV/cm, about 5 to about 150 kV/cm, about 10 to about 140 kV/cm, about 20 kV/cm to about 130 kV/cm, about 30 to about 120 kV/cm, about 40 to about 110 kV/cm, about 50 to about 100 kV/cm, about 60 to about 90 kV/cm, about 70 to about 80 kV/cm.

The electric field can be a function of voltage applied to the membrane and diameter of pores or tubes of the membrane.

Porous membranes as described herein can be part of an electroporation system (also herein referred to as an electroporation system or a system). An electroporation system as described herein can have one or more chambers. An electroporation system as described herein can have a porous membrane between two ends of one or more chambers, and the porous membrane can separate the chamber into two portions. An electroporation system as described herein can have a conductive porous membrane between two ends of one or more chambers, and the porous conductive membrane can separate the chamber into two portions. The two portions of the chamber on either side of membrane can be in fluidic communication and configured so that fluid from one portion of the chamber must pass through the membrane to reach the other portion.

In an embodiment, an electroporation system as described herein comprises a single chamber with a feed portion and a receiving portion, the two portions separated by a porous membrane. In an embodiment, electroporation systems as described herein comprise two separate chambers, a feed chamber and a receiving chamber, which are in fluid communication with one another and are separated by a porous membrane, wherein the contents (which can be a suspension of cells, meaning cells in a solution) of the feed chamber can pass to the receiving chamber through one or more pores in the porous membrane.

A portion of a chamber can be a feed or donor portion or chamber, which cells are placed into. A portion of a chamber can be a receiver portion or chamber which can receive cells that flow from the feed or donor chamber and through the porous membrane. A feed or donor portion or chamber can be a "top" portion or chamber and a receiver portion or chamber can be a "bottom" portion or chamber. A portion or chamber that receives cells that flow through the porous membrane can also be called a collection device. In certain embodiments, cells are placed in a feed chamber in a solution with one or more exogenous agents, where they pass through the membrane into a temperature controlled receiver chamber.

The chamber of the system can be of varying geometries and can be constructed from various materials, for example glass or plastic or plastic polymer. Metal, ceramic, wood, and minerals may also be suitable. In an embodiment, the chamber or chambers of the system is a glass cylinder.

The electroporation system can be configured so that a constant voltage or one or more electric pulses can be delivered to or across the porous membrane to create an electric field gradient of about 1V/cm to about 200 kV/cm. Electric pulses can have a magnitude and a duration, can take on any shape (square, sine, triangle, sawtooth, etc), and can repeat after a duration of time. One skilled in the art would recognize that electric pulses as described herein can be altered in magnitude, duration, shape, and frequency, individually or in combination for a desired application as taught herein.

One portion of the chamber on side of a membrane can contain an electrode. Alternatively, one or more portions on either side of the membrane can each have an electrode (more than one electrode present in the system) to deliver a voltage or electric field gradient across the membrane. In certain embodiments, an electrode can be made of platinum, gold, tin, aluminum, copper, carbon, titanium, brass, silver, palladium, metal oxides, zinc, nickel, lithium, mercury, molybdenum, tungsten, iron, titanium, magnesium, manganese, carbon or other suitable material or combinations thereof.

In certain embodiments, the counter electrode can be in the receiver or feed chamber. In an embodiment, the counter electrode is in the feed chamber and can be a platinum counter electrode.

One or more electrodes can be connected to and in electrical connection with an electric generating device such as a pulse generator, potentiostat or power supply (a DC power supply for example). The electric generating device can further be in electrical connection with the membrane. A wire can be connected to the electric pulse generating device and affixed to a conductive material-coated region of the membrane by way of copper tape or other suitable apparatus. In an embodiment, an electric circuit is formed between a chamber with an electrode, an electric pulse generating device, and the porous membrane and configured so that one or more electric pulses or a continuous voltage are delivered to the conductive material-containing area[s] of the porous membrane. In an embodiment, an electric circuit is formed between a chamber with an electrode, an electric pulse generating device, and the porous membrane and configured so that one or more electric pulses are delivered to the conductive material-containing area[s] of the porous membrane. In an embodiment, an electric circuit is formed between two or more electrodes positioned on opposite sides of a membrane, an electric pulse generating device, and configured so that one or more electric pulses or a continuous voltage are delivered to the electrodes. Pulses or voltages can be positively or negatively charged. Negatively charged voltages or electric pulses in this circuit can prevent oxidation of the conductive material of the conductive porous membrane.

In an embodiment, a chamber is configured so that a porous membrane separates the chamber into two portions on opposite sides of the porous membrane. A portion of the chamber on one side of the porous membrane can be configured to receive cells. In an embodiment, the system is configured so that one portion of the chamber receives cells from outside of the system. The cells can be in the form of an aqueous suspension.

The system can then be further configured so that the cells flow through the pores of the porous membrane, while one or more electric pulses (or a continuous voltage) are applied to or across the porous membrane by the electric generating device, to the other portion of the chamber. Relative to a flat resting planar surface, cells can flow horizontally, vertically, or any other path or combination or paths oriented radially or otherwise in relation to the flat resting planar surface.

The cells in this way can flow through the membrane from one portion of the chamber to the other portion of the chamber. In an embodiment, the portion of the chamber that receives cells that flow through the membrane can be configured to release cells from the system for use in downstream applications. In an embodiment, the portion of the chamber that receives cells that flow through the porous membrane can be in fluidic communication with one or more downstream analysis devices, and configured to send cells that have passed through the membrane to the one or more analysis devices. In an embodiment, the portion of the chamber that receives cells prior to cell flow through can be configured to stir the cells with a stirring device to create a homogenous mixture of cells. In an embodiment, the chamber that receives cells that flow through the conductive porous membrane can be configured to stir the cells with a stirring device to create a homogenous mixture of cells. The stirring device can be a magnetic stir bar, a mechanical stirrer, gas bubbling. In certain embodiments, air bubbling is not used to mix cells and exogenous agents before passing through the porous membrane.

The temperature-controlled receiver chamber can maintain the chamber or solution in the receiving chamber or both at a temperature of about −40° C. to about 200° C., about −30° C. to about 190° C., about −20° C. to about 180° C., about −10° C. to about 170° C., about 0° C. to about 160° C., about 10° C. to about 150° C., about 20° C. to about 140° C., about 30° C. to about 130° C., about 40° C. to about 120° C., about 50° C. to about 110° C., 60° C. to about 100° C., about 70° C. to about 90° C., or about 80° C. In certain embodiments, the receiving chamber can comprise a heating device, such as a hot plate or an incubator to warm that can use fluid or air to warm the chamber and/or solution in the receiving chamber to a temperature above ambient (room) temperature.

In an embodiment, the portion of the chamber that receives cells prior to cell flow through can be coupled to a cooling device that lowers the temperature of the cells to a temperature lower than ambient temperature. In an embodiment, the portion of the chamber that receives cells that flow through the conductive porous membrane can be coupled to a cooling device that lowers the temperature of the cells and/or receiver chamber solution to a temperature lower than ambient temperature. The cooling device can be a container containing an ice bath, configured to hold the portion of the chamber[s] that receive cells in the ice bath without the contents of the cooling device and the portion of the chamber mixing. The cooling device can also be a circulation of cold fluid through a jacket around the chamber, a flow of cold gas, or other suitable ventilation technique.

In an embodiment, the system can additionally comprise a pump that can be configured to draw an aqueous suspension of cells from the first portion of the chamber, through the membrane, and into the second portion of the system. In an embodiment, the system can additionally comprise a vacuum source configured to create vacuum in the system and draw an aqueous suspension of cells from the first portion of the chamber, through the membrane, and into the second portion of the system. In an embodiment, an aqueous suspension of cells can be drawn from one portion of the chamber, through a porous membrane and into the other portion of the chamber by gravity. In an embodiment, the system can additionally comprise a pump that can be configured to send cells from the portion of the chamber that receives cells that have passed through the membrane to one or more downstream analysis devices. In an embodiment, the device further comprises an air flow device that sends air into a portion of a chamber to push cells through the membrane into the other portion. In certain embodiments, the system lacks a pump. In certain embodiments, devices as described herein can be configured with a flow rate of cells from one portion of the device to another portion of the device of about 1 nL/s to about 1 L/s. In certain embodiments, the stirring speed in any portion of the device can be about 0 to about 10000 rpm.

Alternatively, the portions of the chamber of an electroporation system as described herein can be comprised of more than one physically separate chamber in fluidic communication with a membrane in between the more than one physically separate chambers, and configured so that one or more chambers receive cells, the cells flow from the one or more chambers and through the porous membrane, while one or more electric pulses (or a continuous voltage) are applied to or across the porous membrane, and into one or more second chambers. A second chamber can be configured to release cells. In an embodiment, the second chamber contains a stirring apparatus that can be a standard magnetic stir bar. In an embodiment, the system can include a diffusion cell, such as a Franz diffusion cell. In certain embodiments, the system lacks a stirbar.

Other configurations of the device and methods as described herein can be realized as well. A flow-through electroporation system may comprise more than one porous membrane and one or more collection portions or chambers, or receiver portions or chambers. The more than one more porous membrane and one or more collection/receiver portion/chambers of a flow-through electroporation system can be in fluidic communication and be arranged in series, parallel, or both. Additionally, the system can be configured to deliver a continuous voltage or one or more electric pulses to or across more than one membrane of a flow-through electroporation system that comprises multiple membranes. For systems with multiple membranes, different electric applications (continuous voltage or one or more pulses) can occur at or across different membranes, and the system can be configured as such. For systems with multiple membranes and collection/receiver portions/chambers, it can be recognized that initial input to the system can be diverted into multiple flow paths, and can be pooled at the collection stage or kept separate for different purposes. Systems with multiple membranes can have different exogenous agents mixing with cells at each respective membrane, individually or in combination. Features as previously can be applied to one or more membranes or one or more collection/receiver chambers/portions in any number of combinations, and one skilled in the art would recognize how to configure the system for a desired application.

Systems and methods as described herein can utilize a volume of cells of about 1 nL or greater. In certain embodiments, the system can use a volume of cells less than 1 mL.

Also described herein is a method of flow-through electroporation. A method of flow-through electroporation can be carried out on a flow-through electroporation system as described above. Methods of flow-through electroporation using porous membranes as described herein can reversibly electroporate cells, facilitating the uptake of one or more exogenous agents by cells that are otherwise impermeable to the cell membrane and/or wall. Methods of flow-through electroporation using porous membranes as described herein can irreversibly electroporate cells, facilitating cell death by lysis or other mechanisms, such as apoptosis (which relies on transcription and translation of pro-apoptotic genes). Methods as described herein may be adapted to both reversibly and irreversibly electroporate cells. In certain embodiments of the method, a cell is electroporated when it passes through the pore[s] of the membrane.

A suspension of cells to be electroporated can be prepared. A suspension of cells can be an aqueous composition comprising cells and media, or other suitable vehicle for cellular transport through pores of a membrane. A suspension of cells can be an aqueous composition comprising cells, media, and exogenous agent to be introduced into the cell.

The systems and methods described herein can be broadly applicable to a wide variety of cell types. Cells as described herein can be any type of living cell comprising a cell membrane and/or a cell wall. Cells as described herein can be any type of prokaryotic or eukaryotic cell comprising a cell membrane and/or a cell wall. Cells can be gram-positive or gram-negative bacteria, a non-limiting example of which being cells of the genus *Escherichia* or species *Escherichia coli* (*E. coli* as used herein). Cells can be mammalian cells from any mammal species, non-limiting examples of which being: human, rat, or mouse mesenchymal stromal cells (also known as mesenchymal stem cells, or MSCs), embryonic kidney cells, fibroblasts, astrocytes, glia, microglia, oligodendrocytes, hepatocytes, myocytes, cardiomyocytes, adipocytes, endothelial cells, epithelial cells, tumor cells, pericytes, lymphocytes, macrophages, megakaryocytes, erythrocytes, mast cells, granulocytes, neutrophils, basophils, mast cells, neurons, ependymal cells, schwann cells. Origin of cells can be from other organisms than bacteria and mammals, such as algae, plants, yeast, and insects for example. In certain embodiments, cells and methods as described herein do not introduce exogenous agents to *E. coli*.

Systems and methods as described herein can utilize a concentration of cells as described above from a single cell to a concentration of about $10^{15}$ cells/mL. In certain embodiments, systems and methods as described herein can use nucleic acids with a concentration of about $10^1$ cells/mL to about $10^{15}$ cells/mL, about $10^2$ cells/mL to about $10^{14}$ cells/mL, about $10^3$ cells/mL to about $10^{13}$ cells/mL, about $10^4$ cells/mL to about $10^{12}$ cells/mL, about $10^5$ cells/mL to about $10^{11}$ cells/mL, about $10^6$ cells/mL to about $10^{10}$ cells/mL, about $10^7$ cells/mL to about $10^9$ cells/mL, or about $10^8$. In an embodiment, $10^7$ cells/mL are used. In an embodiment, $10^6$ cells/mL are used. In an embodiment, $10^6$ cells in suspension in 100 µL of solution can be electroporated by systems and methods as described herein with plasmid DNA (as described below) at a concentration of about 500 ng/mL.

Exogenous agents as described herein can be an agent that cannot enter a cell by simple diffusion or active transport. Exogenous agents can be agents that are impermeable to a cell wall or membrane. Non-limiting examples of exogenous agents can include small molecules, amino acids, amino acid polymers, proteins, nucleic acids, lipids, polymers, and conjugates of molecules/proteins/nucleic acids/lipids/polymers. Small molecules can include lipids, nucleic acid, or protein dyes. Small molecules can include modulators of enzyme activities. Small molecules can include chemical structures that bind to lipids, proteins, or nucleic acids, individually or in combination or otherwise modulate cellular function without binding to a target. Nucleic acids can include natural or synthetic ssDNA, dsDNA, cDNA, ssRNA, dsRNA, siRNA, mRNA, tRNA, rRNA, miRNA, tmRNA, crRNA, or any other polymer of natural or synthetic nucleobases (non-limiting examples of which include cytosine, guanine, adenine, uracil, and thymine or synthetic derivatives thereof). Nucleic acids can be in the form of one or more plasmids. Plasmids can comprise one or more promoter nucleic acid sequences that promote cell-type specific expression (or translation) of the sequences as well as one or more nucleic acid sequences that code for proteins (which can be mRNA coding sequences, for example), which can be translated and expressed by a cell. Proteins can be any natural or synthetic polymer of amino acids, natural or synthetic derivatives thereof. In certain embodiments, the exogenous agent is not a fluorescent dye.

Systems and methods as described herein can utilize a concentration of nucleic acids as described above of about 1 µg/mL to about 1 g/mL. In certain embodiments, systems and methods as described herein can use nucleic acids with a concentration of about 10 ng/mL to about 500 ng/mL, about 50 ng/mL to about 450 ng/mL, about 100 ng/mL to about 400 ng/mL, about 150 ng/mL to about 350 ng/mL, about 200 ng/mL to about 300 ng/mL, about 10 ng/mL to about 50 ng/mL, or about 250 ng/mL.

Media (also known as vehicle as described herein) can be anything suitable to transport cells or cells and exogenous agents with or through a porous membrane (while a constant voltage or one or more electric pulses are being applied to or across the membrane). Media can allow cells to stay viable and allow exogenous agents to retain their function and exert action inside a cell. Media can contain electrolytes.

Media can be buffered to maintain a pH of about 7.4 or about 7.5 or about 7 to about 8. Non-limiting examples of media that can be used include aqueous media such as: phosphate-buffered saline (PBS), Dulbecco's modified eagle media (DMEM), lysogeny broth (LB broth, aka Luria-Bertani media), nutrient broth, RPMI, biological fluids, tissue extracts, IMDM, peptone water, urease medium, buffered glycerol saline, water, deionized water, water and glycerol, and balanced salt solutions, among others. The media can be anything suitable to form an electric field gradient across the cells in order to increase the permeability of the cell membrane and/or cell wall. One skilled in the art would recognize that selection of media is application-dependent and could choose an appropriate media for the desired application according to the systems and methods herein.

A suspension of cells can be prepared by mixing media or other vehicle and cells to form a composition. In an embodiment, a suspension of cells can be prepared by mixing media, cells, and one or more exogenous agents to form a composition. In an embodiment, a suspension of cells is prepared by centrifuging a volume of media containing cells, pouring off supernatant, resuspending in media or other aqueous solution and mixing. In an embodiment, a suspension of cells is prepared by centrifuging a volume of media containing cells, pouring off supernatant, resuspending in media or other aqueous solution, adding one or more exogenous agents, and mixing. Other techniques can be used in the preparation of a suspension of cells, non-limiting examples of which being cooling, sonication, or filtration.

After the suspension of cells is prepared, the suspension can be passed through a porous membrane as previously described. One or more electric pulses or a continuous voltage can be applied to or across the membrane while the suspension of cells is passed through. The one or more electric pulses or continuous voltage can be adapted to reversibly electroporate, irreversibly electroporate, or both cells.

In an embodiment, a −4V electric pulse with a 30 ms duration is applied by an electric pulse generating device to the porous membrane every 250 ms for the duration of the flow of the cell suspension through the membrane. The one or more pulses can have a magnitude of about 0V to about ±100 kV; about ±500 V to about ±90 kV; about ±1 kV to about ±80 kV; about ±10 kV to about 70 kV, about ±20 kV to about ±60 kV, about ±30 kV to about ±50 kV or about ±40 kV. The one or more pulses can have a magnitude of about 0V to about ±100V, about ±10V to about ±90V, about ±20V to about ±80V, about ±30V to about ±70V, about ±40V to about ±60V, or about ±50V.

The one or more pulses can have a magnitude of about 0V to about ±5V, about ±1V to about ±4V, or about ±2V to about ±3V. The pulse can have a magnitude of about 0V to about −5V, about −1V to about −4V, or about −2V to about −3V. The duration can be about 10 ns to a continuous duration lasting as long as the cells are flowing. The one or more pulses can be applied as long as the cells are flowing or the pulses can have a frequency of about 0.01 to $10^8$Hz. One skilled in the art would recognize that the parameters of the one or more pulses, such as magnitude, duration, and frequency can be altered independently, or in combination, according to the flow, cell type, or specific application. In certain embodiments, a −4V electric pulse with a 30 ms duration is not used. In certain embodiments, pulses with a frequency of 3.6 hz are not used.

Alternatively, a continuous voltage can be used. The duration of a continuous voltage can be the total duration of flow or less. The continuous voltage can have a magnitude of about 0V to about ±100 kV; about ±500 V to about ±90 kV; about ±1 kV to about ±80 kV; about ±10 kV to about 70 kV, about ±20 kV to about ±60 kV, about ±30 kV to about ±50 kV or about ±40 kV. The continuous voltage can have a magnitude of about 0V to about ±100V, about ±10V to about ±90V, about ±20V to about ±80V, about ±30V to about ±70V, about ±40V to about ±60V, or about ±50V. The continuous voltage can have a magnitude of about 0V to about ±5V, about ±1V to about ±4V, or about ±2V to about ±3V. The continuous voltage can have a magnitude of about 0V to about −5V, about −1V to about −4V, or about −2V to about −3V Various methods and/or devices can be used to facilitate flow of the cell suspension through the pores of a conductive porous membrane, non-limiting examples of which being gravity, an air pump, a vacuum source, or a pump, such as a peristaltic pump. Cells that pass through a porous membrane, the membrane having one or more electric pulses applied to or across it, can be subject to an electric field gradient of about 1V/cm to about 200 kV/cm. The electric field can cause disruption of the cell membrane and/or wall of a cell, and can create one or more openings in the cell membrane and/or cell wall that allow exogenous agents that are otherwise impermeable to enter the inside (or be transported to the cytosol) of a cell. FIGS. 1 and 2 are flow charts illustrating embodiments of the method herein.

After the suspension of cells is passed through the membrane, the cells are collected in a collection chamber. Cells in the collection chamber can then be removed from the collection chamber by a variety of means. In an embodiment, cells in the collection chamber can be pumped from the collection chamber through a tube to one or more downstream analytic devices. Non-limiting analytic devices can include UV/vis/fluorescence spectrometers and/or microscopes and electrochemical analyses.

In an embodiment of the method, the suspension of cells can be cooled and/or stirred in the collection chamber during, before and/or after collection (i.e. while, before or after the suspension passes through the membrane). In an embodiment, the cells are stirred with a magnetic stirbar by way of a magnet. In an embodiment, the collection chamber is cooled to a temperature that is lower than ambient temperature. In an embodiment, cells can be cooled to a low temperature by putting them in an ice bath or on ice before putting them in the system. In an embodiment, the collection chamber is cooled to a temperature that is lower than ambient temperature and the cells are stirred in the collection chamber during and/or after collection (i.e. while or after the suspension passes through the membrane). In certain embodiments, a stirbar is not used to stir the cells.

In another embodiment of the method, an additional volume of media is passed through the pores of the porous membrane while one or more electric pulses are being applied to or across the porous membrane and collected in the collection chamber to collect cells that "stuck" to the top of the membrane or pore sides and pass these stuck cells through. The volume of media can be cooled or placed in a cooled portion of a chamber before being passed through the membrane. In another embodiment of the method, an additional volume of media is passed through the pores of the porous membrane while one or more electric pulses or a continuous voltage are being applied to or across the porous membrane and collected in the collection chamber which has been cooled. In another embodiment of the method, an additional volume of media is passed through the pores of the porous membrane while one or more electric pulses are being applied to or across the porous membrane and collected in the collection chamber which has been cooled and the media that passes through the membrane into the cooled collection chamber is stirred.

In another embodiment of the membrane, an additional volume of media is passed through the pores of the porous membrane while one or more electric pulses or continuous voltage are being applied to or across the porous membrane and collected in a second collection chamber, and the contents of the second chamber are passed through the membrane while one or more electric pulses are being applied, and collected into the first collection chamber. In another embodiment of the method, an additional volume of media is passed through the pores of the porous membrane while one or more electric pulses are being applied to or across the porous membrane and collected in a second collection chamber, the contents of the second collection chamber are passed through the pores of the porous membrane and collected into the collection chamber which has been cooled. In another embodiment of the method, an additional volume of media is passed through the pores of the porous membrane while one or more electric pulses are being applied to or across the porous membrane, collected into a second collection chamber, the contents of the second collection chamber are then passed through the pores of the porous membrane while one or more electric pulses are being applied to or across the membrane, and collected in the collection chamber which has been cooled and the media that passes through the membrane into the cooled collection chamber is stirred.

Abbreviations

A.U.: arbitrary units; DI: distilled water; LB: Luria Broth; PBS: Phosphate Buffered Saline; PI: Propidium Iodide; Pt: Platinum; YOPRO: YO-PRO-1 Iodide; EP, electroporation.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Figure 3:
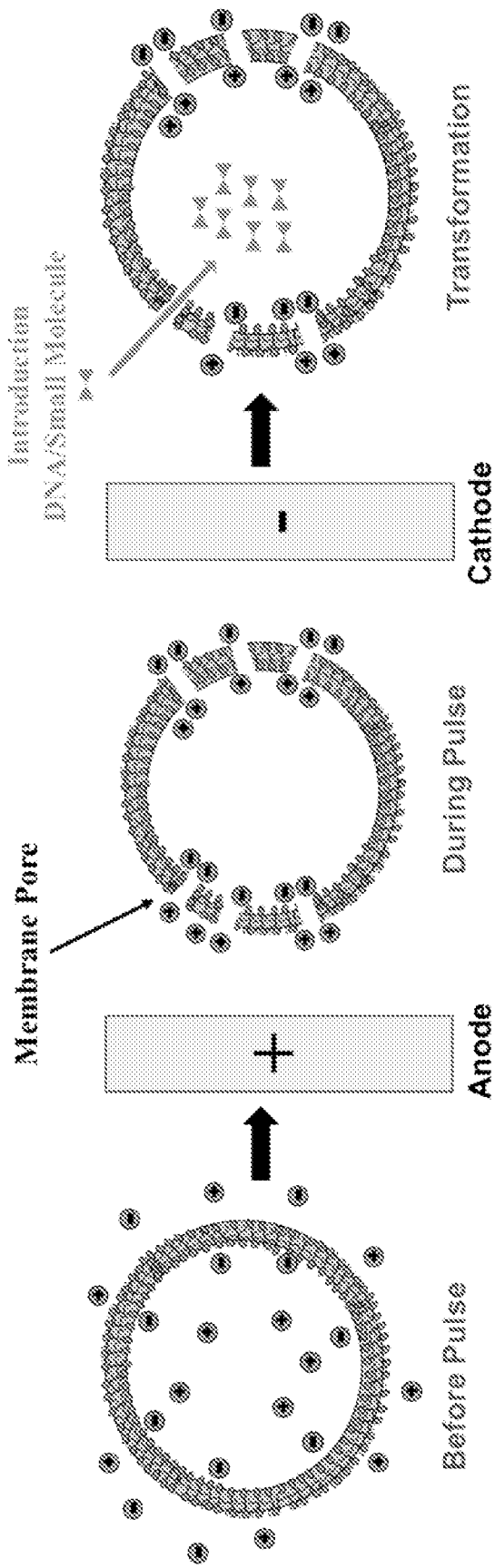
FIGS. 3A-3C depict a general overview of an embodiment of electroporation.

Electroporation is a method used to introduce foreign materials, otherwise impermeable to the cell membrane, into cells by using an applied electric field to create transient pores in the cell membrane. FIG. 3A shows a normal cell at rest. FIG. 3B shows a cell under an applied electric potential high enough to electroporate the cell. FIG. 3C shows the potential to insert DNA or other exogenous agents in the cell after electroporation. An applied electric field, as shown in FIG. 3B, creates openings in the cell membrane that allow foreign substances (that are otherwise cell-impermeable) to cross the cell membrane into the interior of the cell. Conventional electroporation systems utilize cuvettes to load cells between electrodes. Use of cuvettes creates a millimeter-scale gap between electrodes, necessitating a large voltage (in the kilovolt magnitude) to suitably electroporate cells in the cuvette. Large electric fields such as these are problematic for cell physiology, and adversely affect cell viability through mechanisms such as Joule heating, intracellular pH changes, and metal ion dissolution.

Figure 4:
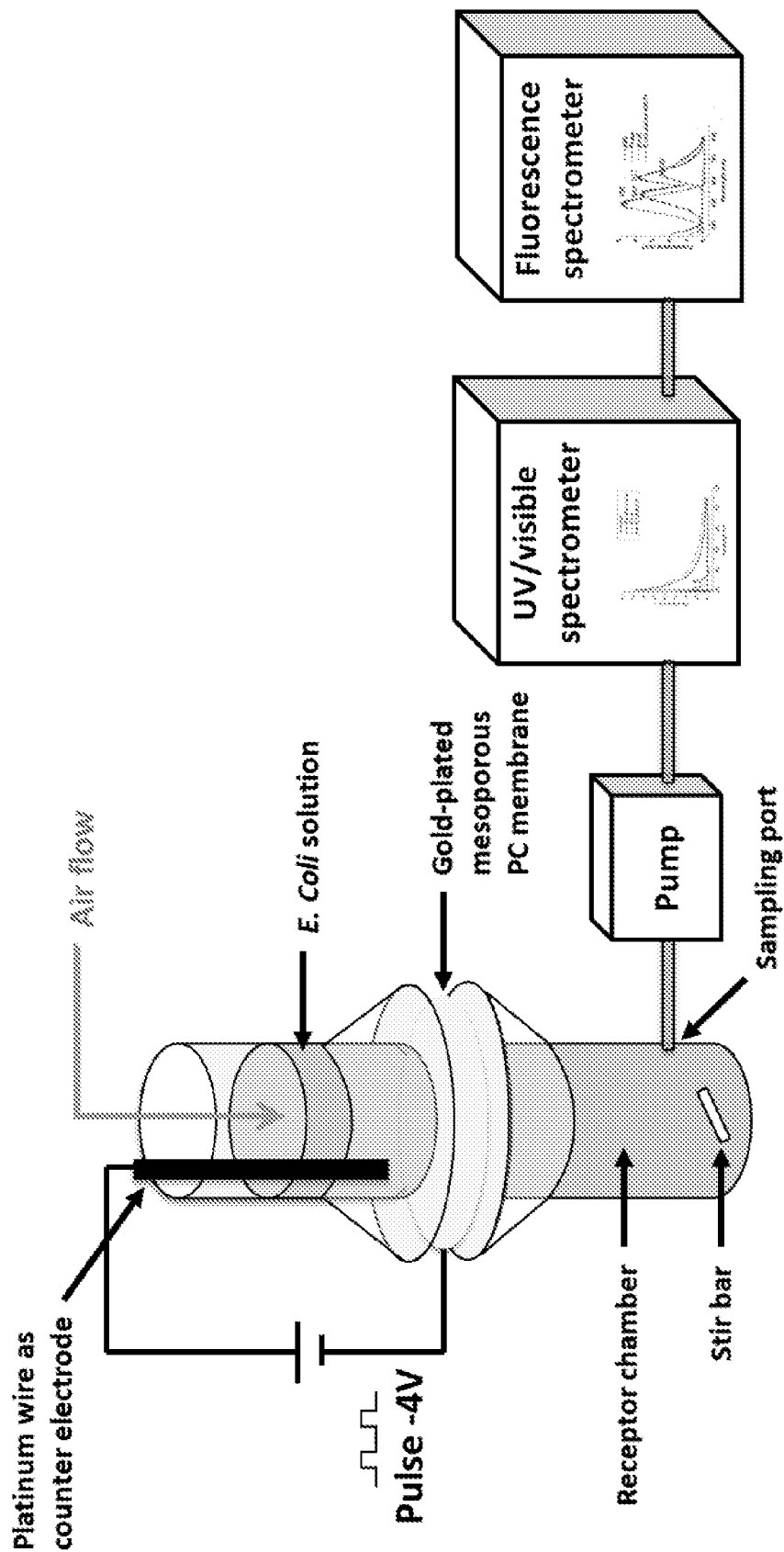
FIG. 4 is an embodiment of an electroporation system and method according to the present disclosure.

FIG. 4 illustrates an embodiment of a flow-through electroporation system according to the present disclosure. Briefly, the embodiment utilizes a microporous (or mesoporous) gold-plated membrane to which a voltage is applied. Cells to be electroporated flow from the top of the system, through the membrane where they are electroporated, and into the collector chamber at the bottom of the system. After electroporated cells pass through the membrane, they can be transferred from the receptor chamber for use in other downstream applications, such as UV/vis spectrophotometer and fluorescence spectrometer analysis.

Figure 5:
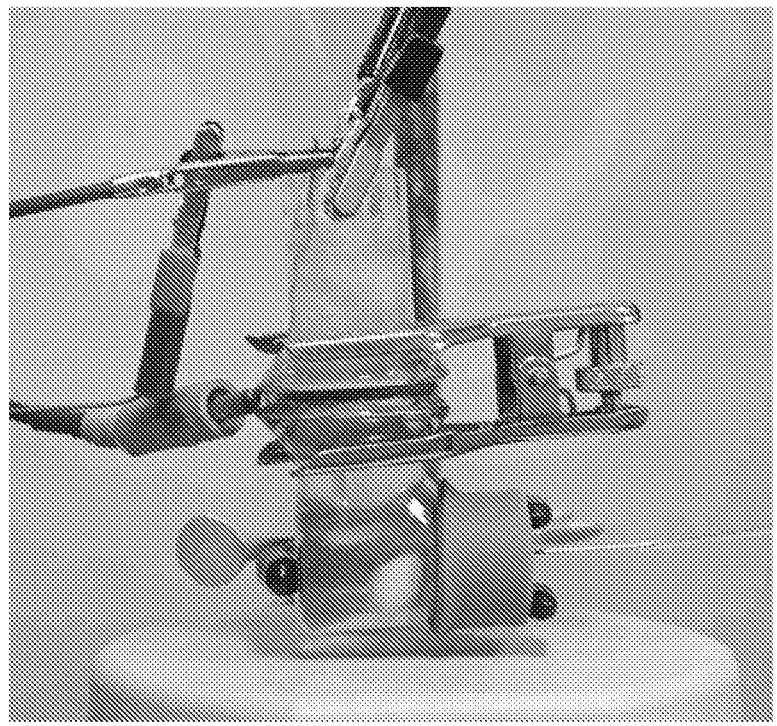
FIG. 5 is an embodiment of an electroporation system according to the present disclosure.
Figure 6:
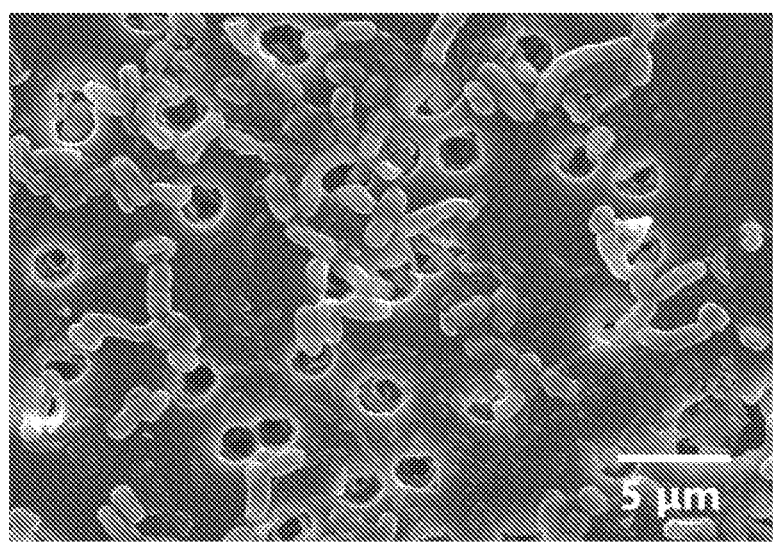
FIG. 6 is an electron micrograph depicting cells on a porous membrane according to the present disclosure, in pores of the membrane, and passing through pores of the membrane.
Figure 7:
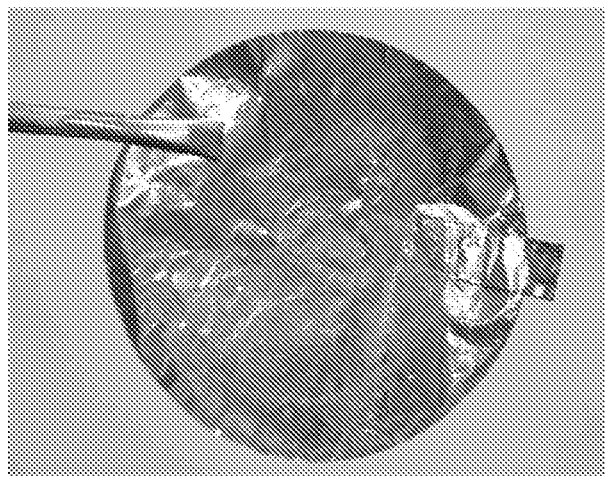
FIG. 7 depicts an embodiment of a conductive porous membrane of the present disclosure.

FIG. 5 is a photograph demonstrating an embodiment of a flow-through electroporation system as described herein. FIG. 6 is an electron micrograph showing cells on the membrane surface and in the pores of the membrane FIG. 7 shows an embodiment of a gold-plated mesoporous polycarbonate membrane according to the present disclosure.

Figure 8A:
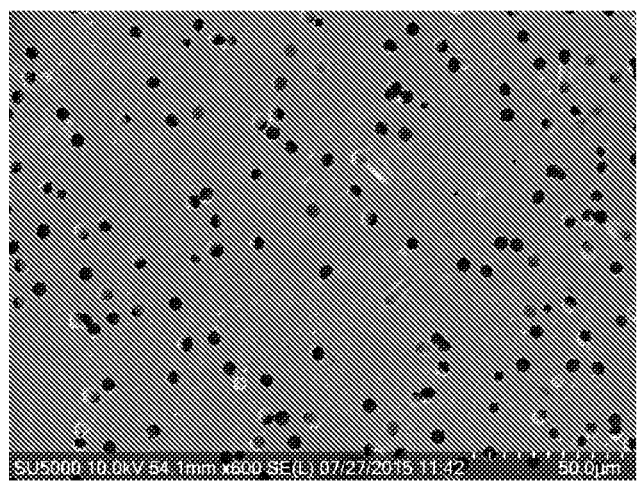
FIGS. 8A-8B are electron micrographs depicting pores (also referred to herein as tubes) of an embodiment of a porous membrane according to the present disclosure.
Figure 8B:
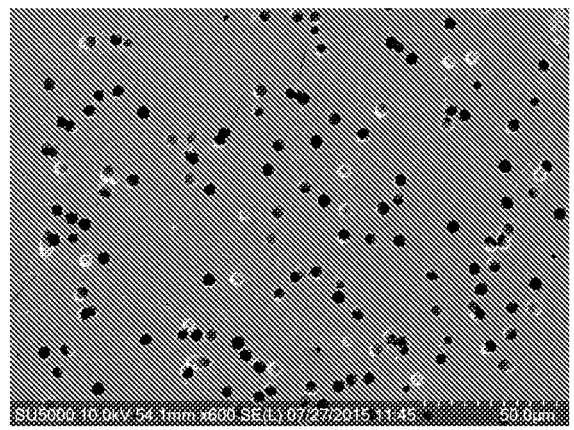

FIGS. 8A and 8B are electron micrographs showing pores of embodiment of a microporous or mesoporous membrane according to the present disclosure. The pores (aka microtubes) can have an average diameter of about 5 μm as shown in FIGS. 8A-8B.

Figure 9A:
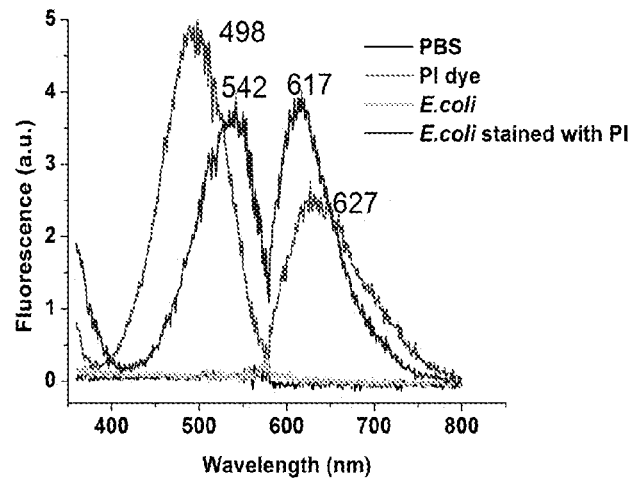
FIG. 9A shows fluorescence excitation and emission spectra of PBS, propidium iodide (PI) dye, E. coli, and E. coli stained with PI.

FIG. 9A shows fluorescence excitation and emission spectra of an electroporation experiment with *E. coli* and PI according to the systems and methods described herein. Fluorescence excitation and emission readings at different wavelengths are shown for PBS (media), PI (media+PI dye), *E. coli* without dye, and *E. coli* with PI.

Figure 9B:
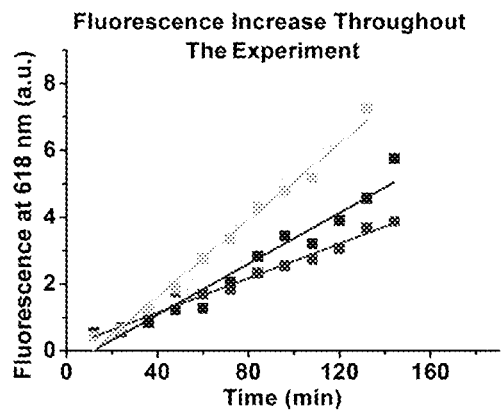
FIG. 9B shows intensity of fluorescence emission across time of electroporation experiments using an embodiment of an electroporation system at different voltages as described herewithin.

FIG. 9B demonstrates the increase in PI fluorescence signal throughout the course of an electroporation experiment for electroporation at −1V (bottom line), −3V (middle line), and −4V (top line).

Figure 9C:
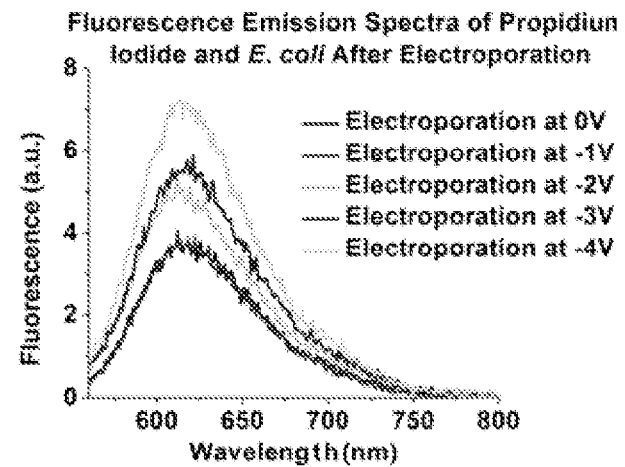
FIG. 9C depicts fluorescence emission spectra of E. coli with PI with an embodiment of the present flow-through electroporation system at different voltages.

FIG. 9C shows fluorescence emission spectra of *E. coli* after electroporation with PI at different voltages, from 0V down to −4V.

Example 2

1. Introduction

When a living cell is placed in a solution containing a large electric field gradient, the voltage difference across the cell membrane can become high enough that pores form in the membrane—electroporation (EP).[1] First studied by Stampfli in 1958,[2] EP now has many applications in medicine and biotechnology including food pasteurization,[3] electrochemotherapy,[4] and the delivery of exogenous DNA into bacteria for transformation.[5] Depending on the application, EP may be reversible, meaning the pores close after some time, or irreversible, which results in cell death.

Currently available EP devices use voltage pulses in the kV range in order to achieve electric field gradients across the cell membrane high enough to porate the cell, for example 3.65 kV cm$^{-1}$ for *Escherichia coli*.[6] Such large voltage pulses are undesirable because they require special safety precautions and complicated experimental procedures.[7] Pulses in the kV range can also be detrimental to reversible electroporation because they produce high cell mortality due to Joule heating, unwanted solution pH changes and metal ion dissolution.[8]

As a result, there is considerable research interest in developing new EP devices that can achieve high electric field gradients with voltage pulses that are orders of magnitude smaller.[9] Devices based on micro-fabricated electrodes[10] and constrictions in microfluidic channels[11] have been proposed to focus the electric field gradient near the cell surface. An alternative approach entails using membranes with microscopic pores with large applied electric field gradients at the pore openings.[12] Such microscale EP devices not only allow for smaller voltage pulses but can provide higher transformation efficiencies, good cell viability and improved spatial and temporal control.[13, 14]

Described herein is a new EP device that can use a commercially available membrane filter with gold microtubes deposited in the pores. Because the tubes can be electronically conductive, they can be electrically charged by applying a voltage in an electrolyte solution.[15, 16] This voltage-charging phenomenon[16] causes an electric field gradient to be developed down the length of the tubes spanning the membrane.

This gradient can be used to electroporate *E. coli* as the cells pass through the membrane. Importantly, the 3.65 kV $cm^{-1}$ which can electroporate *E. coli*[6] can be achieved by applying voltage pulses of only 4 V to the microtube membrane. This is roughly 3 orders of magnitude smaller than used in typical commercial EP devices. High electric field gradients are achieved at low voltages with this device because the membrane filter housing the microtubes is only 10 µm in thickness.

The percentage of reversibly and irreversibly electroporated bacteria were investigated as a function of the magnitude and frequency of the voltage pulses, as well as the diameter of the microtubes in the membrane.

2. Results and Discussion 2.1. Gold-Microtube Membranes

Figure 10A:
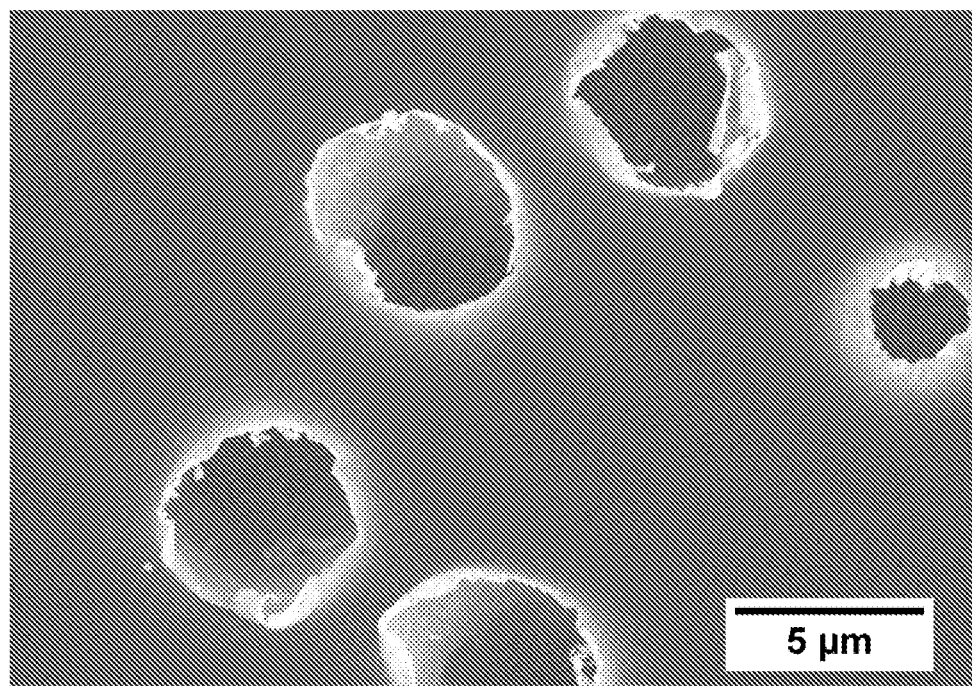
FIG. 10A-10B are electron micrographs of an embodiment of a gold porous membrane according to the present disclosure.

Polycarbonate filter membranes with a thickness of 10 µm and cylindrical pores of diameter ranging from 3 to 20 µm were used (FIG. 23). The electroless method used to plate gold tubes within the pores has been described previously.[17, 18] This method yields the gold tubes and thin (~100 nm) gold films on both faces of the membrane. One of the gold surface films (FIGS. 10A-B) was removed.[18] Ohmic contact was made to all of the gold microtubes in parallel through the other (lower) gold film.

Figure 10B:
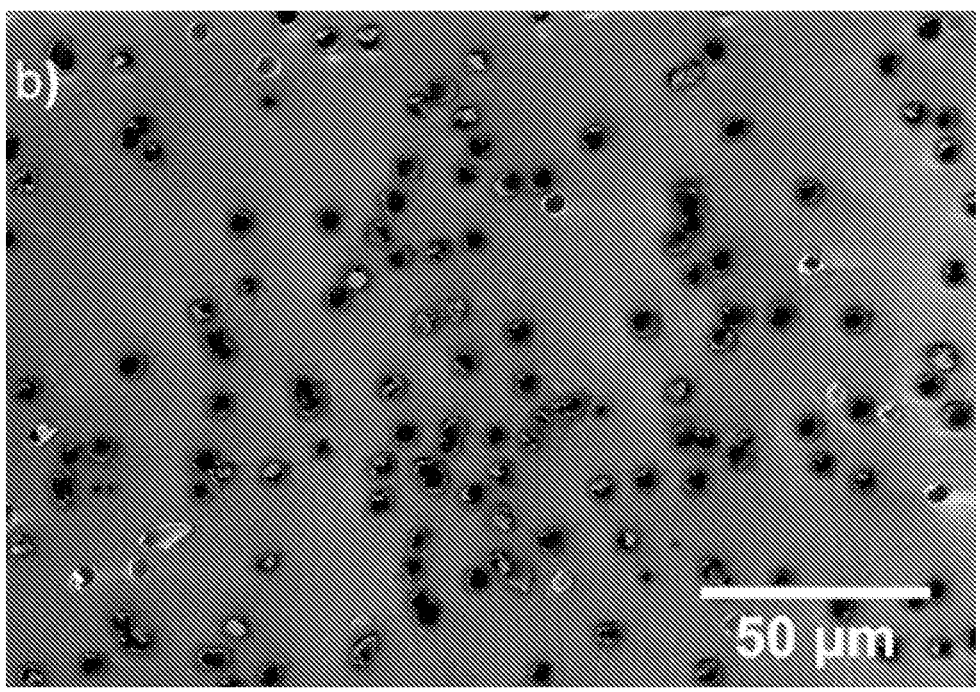

Images like FIG. 10B were used to obtain the inside diameters of the gold microtubes. The tube wall thickness (100±30 nm) was also obtained from such images. Most of the EP data herein were obtained from membranes with inside tube diameters of 5.1±0.3 µm and tube density of $5\pm1\times10^5$ $cm^{-2}$. EP data were also obtained for membranes containing 3 µm, 10 µm and 20 µm diameter gold tubes.

2.2. Flow-Through EP Cell

Figure 11:
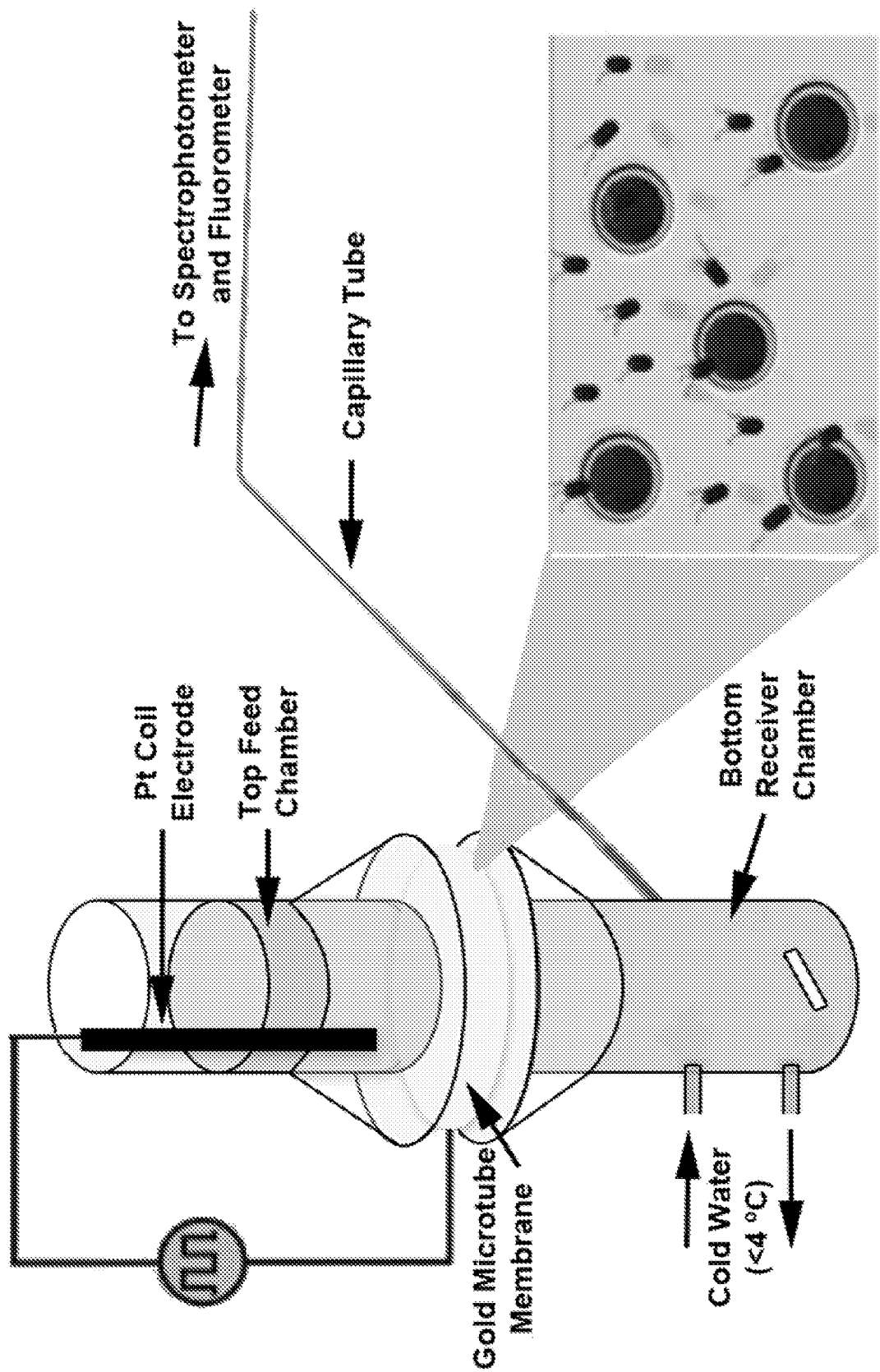
FIG. 11 is a schematic depicting an embodiment of an electroporation system according to the present disclosure.

The gold-microtube membrane was mounted in a Franz diffusion cell, separating the upper feed chamber from the lower receiver chamber (FIG. 11). Three milliliters of a solution of $2\times10^8$ *E. coli* $mL^{-1}$ in phosphate buffered saline (PBS) (pH=7.5) were added to the upper chamber. The lower chamber contained 12 mL of PBS. A peristaltic pump was used to pull the feed solution containing the *E. coli* through the membrane, into the receiver chamber, and then through a UV-visible spectrophotometer for analysis (FIG. 11). The inset in FIG. 11 gives a depiction of the relative sizes of the bacteria and the openings of the gold microtubes for a membrane with 5 µm diameter tubes. The represented bacteria have a diameter of 1 µm and a length of 2 µm.

While the bacteria-containing feed solution was in transit through the membrane, square-wave voltage pulses were applied between the gold film on the membrane bottom surface and a platinum coil counter electrode in the upper feed chamber (FIG. 11). The pulse duration was 30 ms for all experiments. This value was chosen based on prior work.[19] The effect of magnitude of the voltage pulses on EP efficiency was investigated over the range of 0 V (no pulse) to −5 V, where the minus sign indicates that the microtube membrane was the cathode. A value of −4 V was used for the majority of the data presented here. The effect of pulse frequency was investigated over a range of 1 to 7.7 Hz. A value of 3.6 Hz was used for the majority of the data presented herein.

2.3. Analysis of the Bacteria

The objective of the present study was to determine the percentages of non-electroporated, irreversibly electroporated (dead) and reversibly electroporated (living) bacteria that had passed through the membrane. Two methods were used. The first was based on flow-through absorbance and fluorescence intensity measurements (flow-through method, FIG. 11). The second method was based on fluorescence microscopy.

Figure 12A:
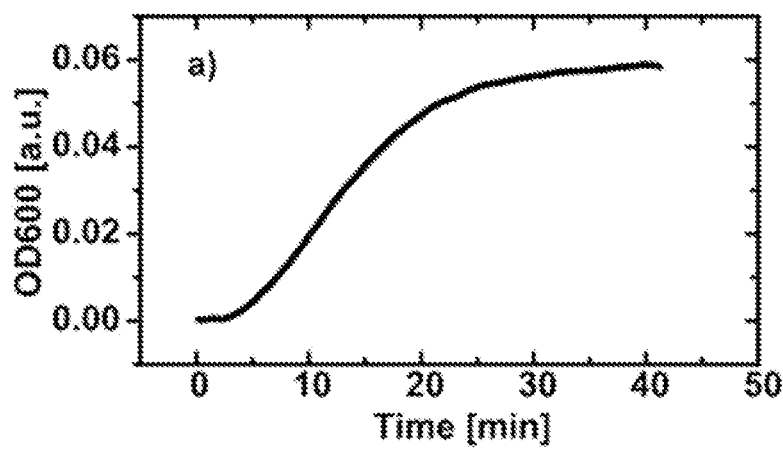
FIG. 12A shows optical density measurements at 600 nm of samples from the receiving chamber of an embodiment of a flow-through electroporation system according to the present disclosure.
Figure 12B:
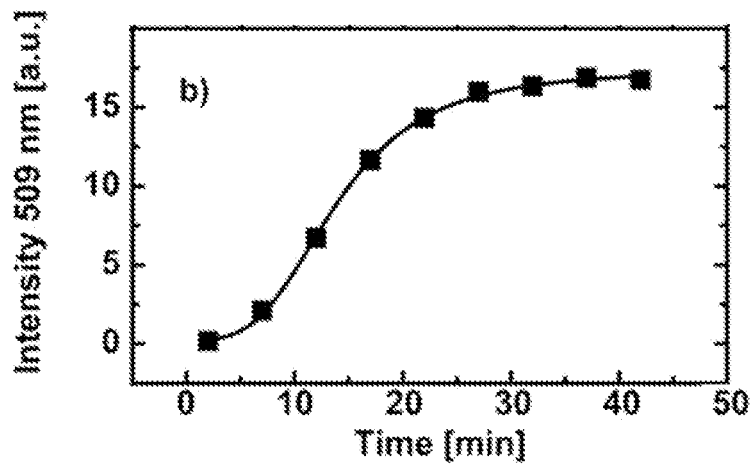
FIG. 12B shows fluorescence emission intensity of YO-PRO-1 iodide (YOPRO) at 509 nm after excitation at 491 nm of samples from the receiving chamber of an embodiment of a flow-through electroporation system according to the present disclosure.
Figure 12C:
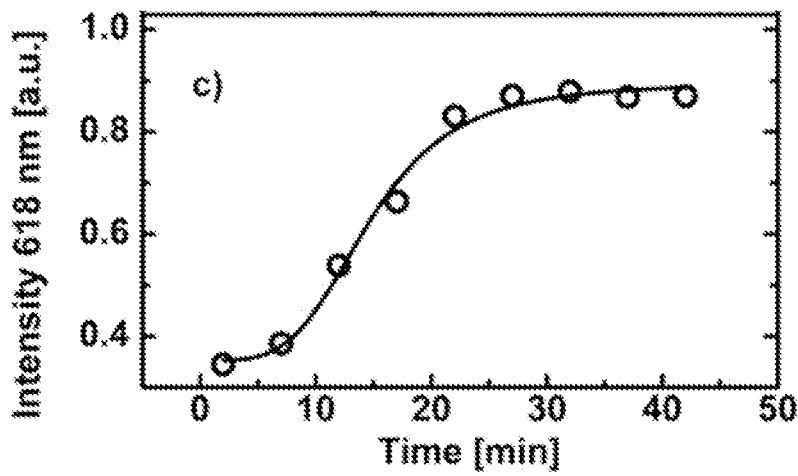
FIG. 12C shows fluorescence emission intensity of PI at 618 nm after excitation at 540 nm of samples from the receiving chamber of an embodiment of a flow-through electroporation system according to the present disclosure.

FIG. 12 shows data from the flow-through method. FIG. 12A presents the optical density of the receiver solution at 600 nm (OD600) during the time course of an EP experiment. The membrane contained 5 µm diameter gold tubes, and −4 V pulses were applied during the experiment. The OD600 allowed for the determination of the total number of bacteria that passed through the membrane.[20] It showed little increase during the first 5 min due to the dead volume between the receiver chamber and the spectrophotometer. From 5 to 30 min the number of bacteria increased as the feed solution was pumped through the membrane. The OD600 leveled at longer times indicating all of the feed solution had passed through the membrane.

A DNA-staining fluorescent probe, YO-PRO-1 Iodide (YOPRO), was used to determine how many of the total number of bacteria that passed through the membrane had been electroporated.[21, 22] YOPRO was added to both the feed and receiver solutions, and the bacteria were exposed to YOPRO during the entire experiment. YOPRO's quantum yield is low when not bound to DNA, but goes up by a factor of 200 when bound.[23]

However, YOPRO can only access the bacterial DNA if the cell membrane has been either permanently or transiently disrupted. Therefore, the appearance of YOPRO fluorescence in the receiver solution (FIG. 12B) shows that EP occurred in our gold-microtube-based device. The fluorescence intensity of YOPRO allowed for the determination of the number of bacteria electroporated.

Of these bacteria that were electroporated, a fraction was dead (irreversibly electroporated) and the remainder was alive (reversibly electroporated). In order to differentiate between the two, a second membrane impermeable fluorescent probe, propidium iodide (PI), was added 30 min after the bacteria solution had been passed through the membrane.[21, 24] This allowed the transiently created (reversible) pores in the viable bacteria to close before PI was added. As a result, only irreversibly electroporated bacteria contained PI, and the fluorescence intensity at 618 nm (FIG. 12C) allowed for the determination of the number of these, now dead, bacteria.

In summary, bacteria that were irreversibly electroporated (dead) showed both green (YOPRO) and red (PI) fluorescence, and bacteria that were reversibly electroporated (alive) showed only green fluorescence.[21, 22] Bacteria that emitted no fluorescence after passing through the membrane were assumed to be alive and not electroporated. An example of the calculations used to obtain the percentages of each type of bacteria is given in the Supporting Information. The fluorescence-microscopy method entailed placing a drop of the receiver solution after the EP experiment onto a microscope slide and first taking a bright-field image so that all of the bacteria (electroporated and non-electroporated) could be counted. A fluorescence image was then obtained to determine which bacteria contained both YOPRO and PI and which contained only YOPRO (FIGS. 20A-20F, see Experimental section).

2.4. Effect of Magnitude of the Voltage Pulses

FIGS. 20A-20F shows representative fluorescence micrographs of samples of the receiver solution after experiments with the indicated magnitudes of voltage pulses. A greater number of red/orange (irreversibly electroporated) and green (reversibly electroporated) bacteria are observed at the highest magnitude of voltage pulses used in these studies, −5

V. Images like these were used to quantify the percentages of each type of bacteria in the sample for the different voltages used.

Figure 13:
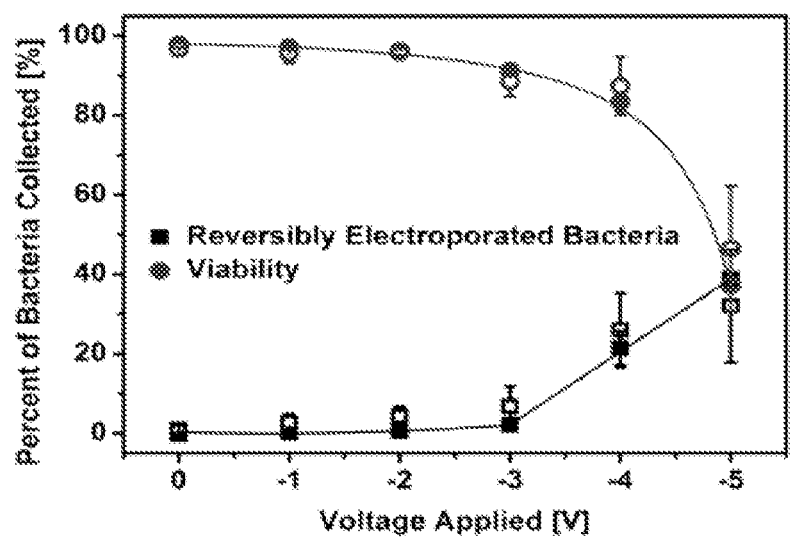
FIG. 13 depicts the average percent of reversibly electroporated bacteria and viability that have passed through the membrane as a function of the magnitude of the voltage pulses applied.

FIG. 13 (lower curves) shows the effect of the magnitude of voltage pulses on the percent of bacteria reversibly electroporated. Data from both the flow-through and fluorescence-microscopy methods show that negative voltage pulses exceeding 3 V were required to achieve optimal EP. EP increases with magnitude of pulses above this limit.

The upper curve in FIG. 13 shows the effect of the magnitude of the voltage pulses on the percent of bacteria that remained alive, either non-electroporated or reversibly electroporated, after passing through the membrane. The filled (solid) squares and circles have been calculated from the measurements of fluorescence intensity and absorbance with spectrometers. The open (hollow) squares and circles have been obtained by manually counting the green, red and non-fluorescent cells in fluorescence and bright-field microscope images. Good agreement between the flow-through and fluorescence-microscopy methods is observed for both the viability and the percentage of reversibly electroporated bacteria analyses (FIG. 13).

2.5. Simulation of Electric Field Gradients

Garcia et al. have recently made careful measurements of the effect of electric field gradients on the extent of EP for *E. coli* and other bacteria.[6] They found that, for *E. coli*, a threshold electric field gradient of 3.65±0.09 kV cm$^{-1}$ can be achieved to accomplish optimal EP. COMSOL 5.0 was used to simulate the electric field gradients in solution in and near a gold microtube to see if gradients of this magnitude could be achieved with membranes as described herein. The tube diameter was 5 μm, and the length of the tube was 10 μm, equivalent to the thickness of the filter membrane. COMSOL's Electrostatics and Transport of Diluted Species 2D-axisymmetric model was used, solving for the electric potential in Poisson's equation.[25]

Figure 14A:
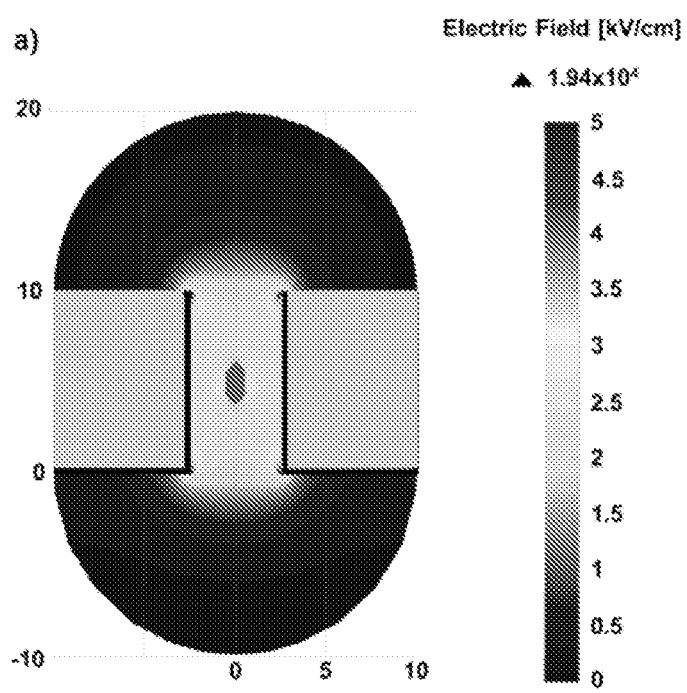
FIG. 14A is an illustration of the electric field distribution simulated using COMSOL in a microtube of an embodiment of a porous membrane of the present disclosure.
Figure 27:
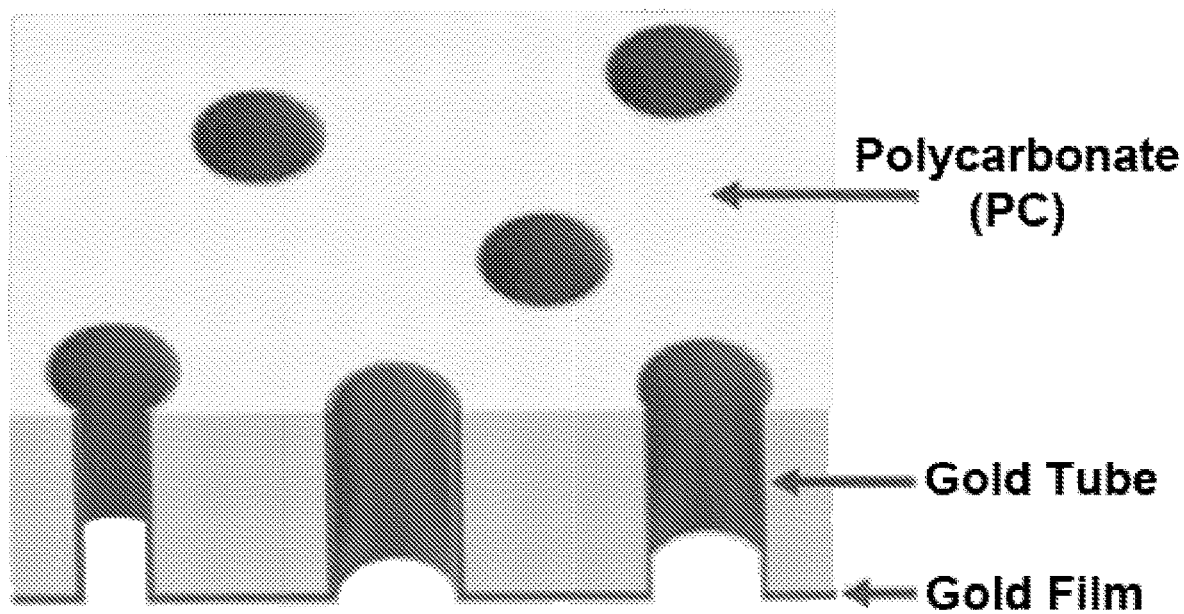
FIG. 27 depicts a schematic illustration of an embodiment of a coated porous membrane according to the present disclosure.

A typical simulation is shown in FIG. 14A. The electrolyte-filled microtube is between the two black vertical lines, which represent the gold tube walls. The lower black horizontal lines represent the gold film on the bottom of the membrane to which the voltage is applied (FIG. 27). The light gray regions around the tube represent the filter membrane. An *E. coli* bacterium (1 μm×2 μm) was placed in the center of the tube (dark grey).

The curved blue zone above the membrane represents the bulk electrolyte solution in the feed chamber containing the counter electrode. In the simulation, the upper edge of this solution is at ground. The curved blue region below the membrane represents the bulk electrolyte solution in the receiver chamber. The voltage used in this simulation was −4 V where experimentally significant reversible EP is observed (FIG. 13).

The colors of the solution in and around the tube represent the electric field gradients (see color code on right of FIG. 14A). The simulation shows that the highest electric field gradients (>5 kV cm$^{-1}$) are observed just inside the upper and lower openings of the tube. In 3D, this would look like high gradient rings in the openings of the tube. High gradients are observed at the tube openings due to the well-known edge effect.[26]

In these regions, the electric field gradient is well above the threshold for optimal EP.[6] However, since these high gradient regions extend only 100 nm from the tube wall, not all bacteria transiting the tube access these regions. Furthermore, bacteria that do access these high gradient regions are more likely to be irreversibly porated.

In most of the inner tube solution the electric field gradient is smaller, −3 kV cm$^{-1}$, as indicated by the yellow/green color. This gradient results because the voltage at the lower gold film, where the pulse is applied, is 3 V more negative than at the tube opening at the upper surface of the membrane. This 3 kV cm$^{-1}$ gradient value is close to the optimal electroporation threshold value for *E. coli* reported by Garcia et al.[6]

However, the simulation suggests that higher gradients, −4 kV cm$^{-1}$, are present immediately around the *E. coli* near the top and bottom of the bacterium (FIG. 14A). These higher gradient rings can result because the ionic current in the tube must be deflected around the bacterium.[13] Since 4 kV cm$^{-1}$ is above the optimal EP threshold for *E. coli*, this simulation suggests, in agreement with experimental data (FIG. 13), that EP should be observed with voltage pulses of −4 V.

Figure 14B:
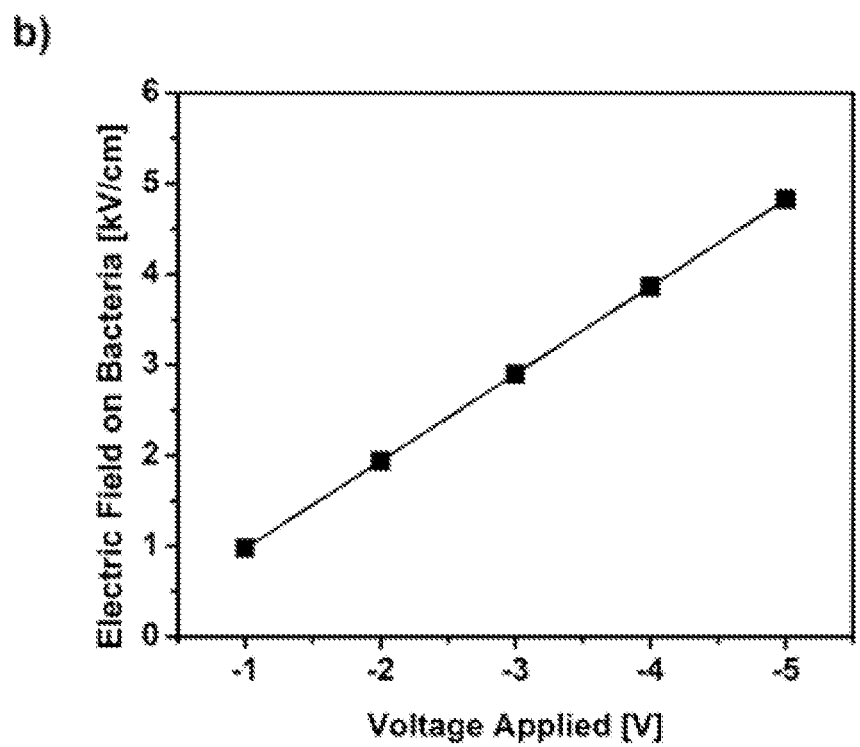
FIG. 14B depicts a COMSOL simulation of the maximum electric field gradient at the surface of a cell located in the middle of pore as a function of the voltage applied.

To explore this issue further, analogous simulations were run with applied voltages in the range from −1 to −5 V. FIG. 14B shows a plot of the highest gradient observed in the rings of solution around the bacterium as a function of the voltage. Again, in agreement with experimental data herein, the simulations show that optimal EP could be observed at applied negative voltages of 4 V or higher. Although optimal EP can occur at negative voltages of 4 V or higher, EP is observed at lower voltages, and could likely be due to the fraction of transiting bacteria that access the very high gradient regions at the openings of the tube.

2.6. Effect of Tube Diameter

Figure 15A:
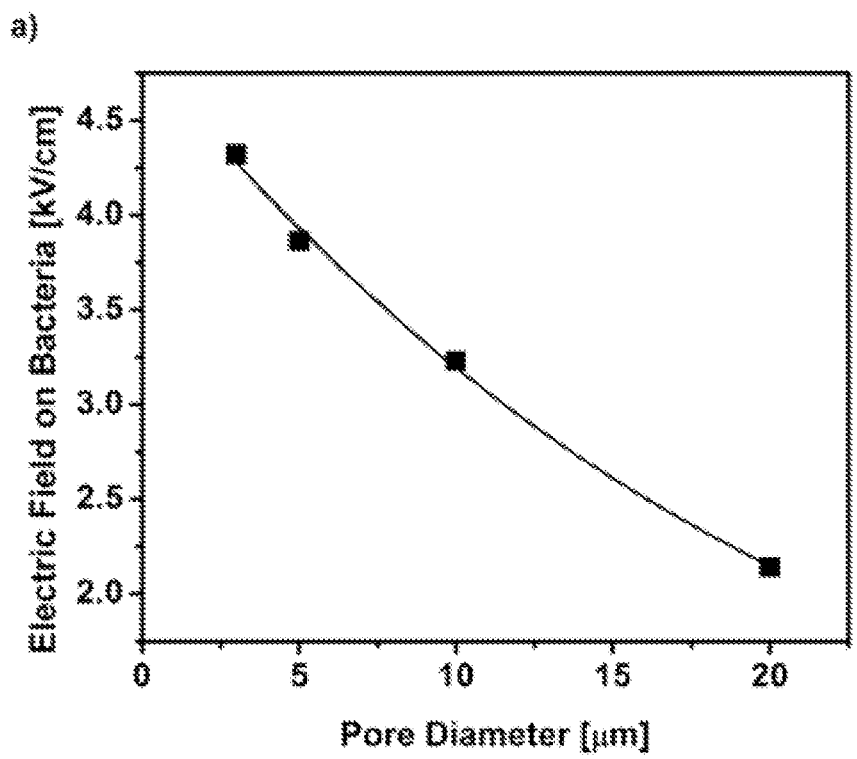
FIG. 15A shows a COMSOL simulation of the maximum electric field at the surface of a cell located in the middle of the pore as a function of average pore/tube diameter

FIG. 15A shows results of analogous simulations for gold microtubes with diameter in the range of 3 to 20 μm. As per FIG. 6, the voltage was −4 V, and the y-axis is the highest gradient observed in the rings of solution around the bacterium for each tube diameter. Because the ionic resistance in the tube decreases with increasing tube diameter, the calculated gradient likewise decreases with tube diameter. These data suggest that extent of EP should decrease with increasing tube diameter, and this is what is observed experimentally in FIG. 15B.

Figure 15B:
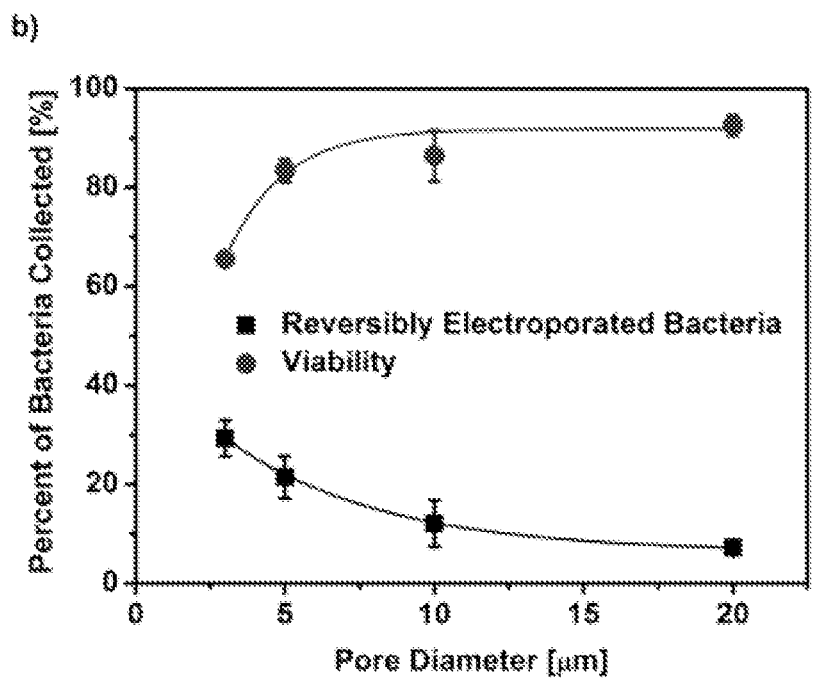
FIG. 15B depicts the average percent of reversibly electroporated bacteria and viability that have passed through the membrane as a function of the average diameter of the pore/tube of a membrane of the present disclosure.
Figure 16:
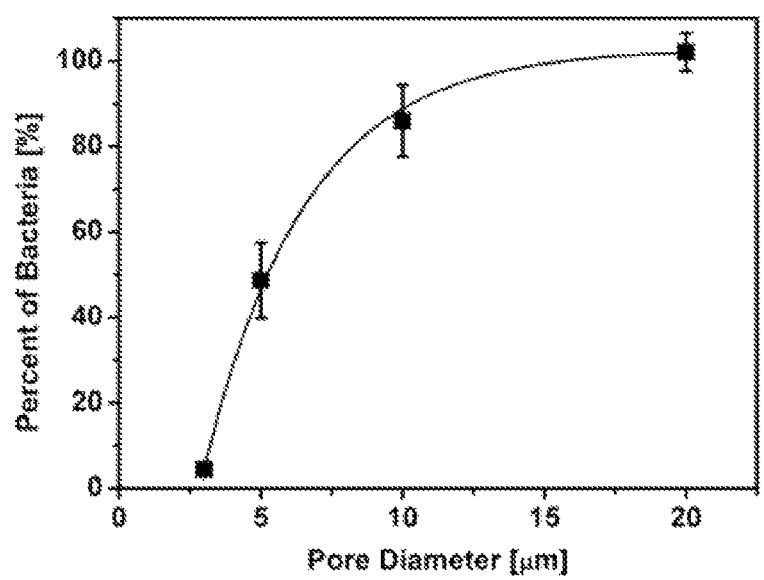
FIG. 16 shows the percentage of total bacteria that pass through the membrane as a function of average pore diameter.

While the experimental and simulated data in FIGS. 15A-15B suggest that smaller diameter tubes are better for EP, there is a limit in that ultimately the diameter is too small to allow the bacteria to pass through the membrane. The issue was explored by determining the percentage of bacteria that pass through the membrane as a function of tube diameter (FIG. 16).

Finally, because only 50% of the bacteria pass through the membrane with 5 μm diameter tubes (FIG. 16) it would seem that this would limit the efficiency of EP. However, we have shown that the bacteria trapped on the surface can be resuspended by adding 4 mL of cell-free buffer, and pulling this solution through the membrane results in 95% of the bacteria being collected.

2.7. Effect of Frequency of the Voltage Pulses

The average time required for a bacterium to transit the microtube membrane can be calculated from the known solution flow rate, assuming that the bacterium does not interact with the tube walls as it transits. An average transit time of 80 ms was determined through this method. The data presented so far were obtained by applying a 30 ms voltage pulse every 250 ms (3.6 Hz). This means that each electroporated bacterium received only one voltage pulse during transit, and that many bacteria received no pulses as they transited in the 250 ms interval before the next pulse. Indeed, with this voltage pulse sequence only 32% of the transiting bacteria would receive a pulse. However, this number is only an approximation because it assumes no interaction between the bacteria and the tube walls, and it is well known that *E. coli* adsorb onto gold surfaces.[27] This analysis suggests that lowering the time interval between pulses, or increasing the pulse frequency, would allow for a larger percentage of bacteria to receive a pulse during transit, and this should increase the percentage of *E. coli* electroporated.

Figure 17:
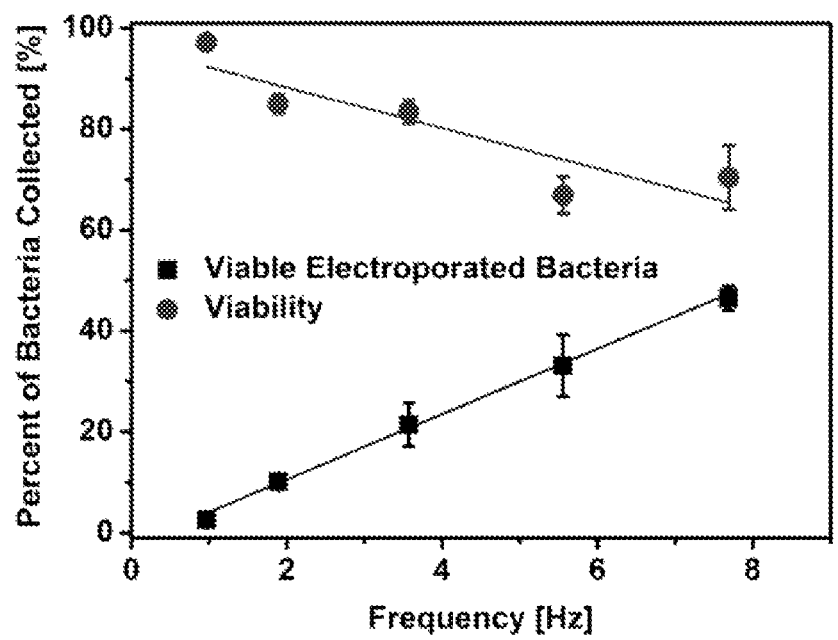
FIG. 17 shows the average percentages of viable electroporated bacteria and viability as a function of the frequency of the electric pulses applied to the membrane.

FIG. 17 shows the effect of pulse frequency on the percent of bacteria reversibly electroporated (lower line) and the percent of viable bacteria (upper line). As expected, the percent of reversibly electroporated bacteria increases with pulse frequency. However, gas bubbles evolved at the membrane surface at frequencies above 5 Hz. Above 8 Hz, gas evolution was vigorous, resulting in the blockage of the membrane's microtubes and the cessation of the flow. In addition, the percent of viable bacteria decreases with increasing frequency (FIG. 17).

2.8. Comparison With a Commercial EP Device

Figure 18A:
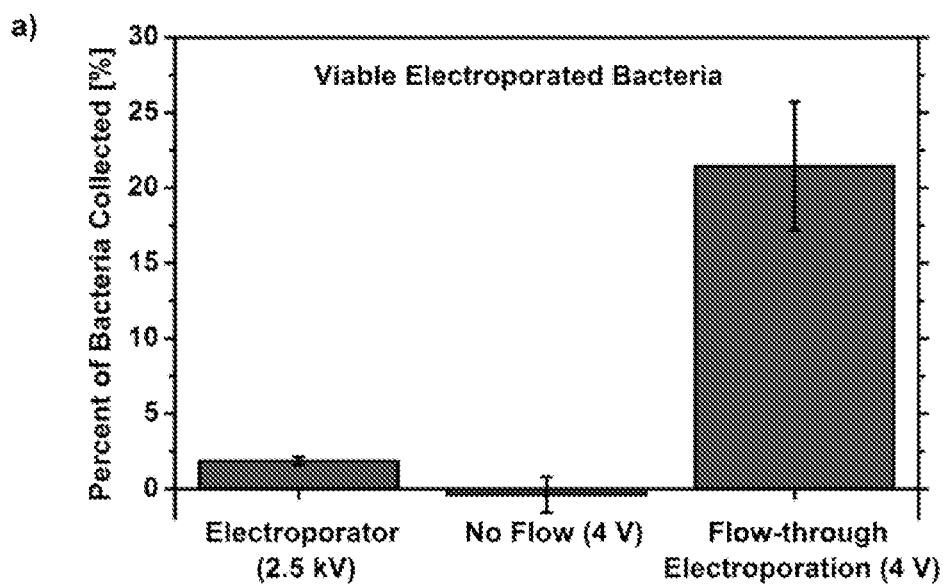
FIG. 18A illustrates the average percentages of reversibly electroporated bacteria with a commercial electroporater using a 2 mm gap cuvette at 2.5 kV, an embodiment of the present electroporation system without flow at −4 V, and an embodiment of the present electroporation system with flow at −4 V.
Figure 18B:
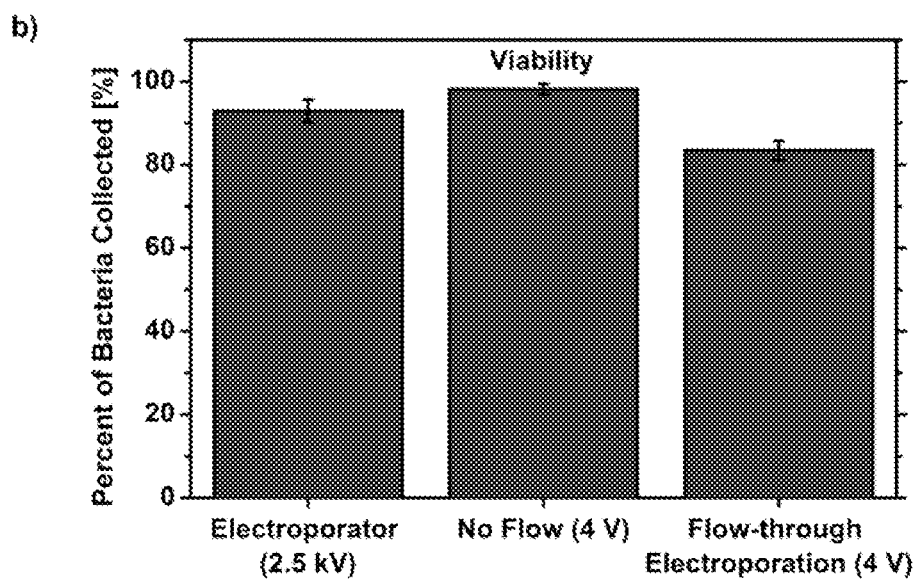
FIG. 18B illustrates the average percentages of viabilities obtained in 2 mm gap cuvettes with a commercial electroporator applying 2.5 kV, an embodiment of the present electroporation system without flow at −4V, and an embodiment of the present electroporation system with flow-through at −4V.

With commercial electroporators, the large electric field gradient required for electroporation is generated by applying a high voltage pulse, around 2.5 kV, to a cuvette enclosing two planar electrodes separated by a 2 mm gap.[17] In contrast, the system described herein employs a gold-microtube membrane to generate similar electric field gradients using low voltage pulses (about 500 times lower voltage than other commercial devices). A comparison of the percentages of viable electroporated bacteria and viability between the system described herein using −4 V pulses and a commercial electroporator is shown herein (FIGS. 18A-18B). FIGS. 18A-18B show average percentages of reversibly electroporated bacteria (FIG. 18A), and viabilities obtained in 2 mm gap cuvettes with a commercial electroporator applying 2.5 kV (FIG. 18B); in an embodiment of the system herein applying −4 V pulses without flow of bacteria through the membrane; and in and embodiment of the flow-through electroporation system applying −4 V.

As a reference, a comparison between the system described herein, utilizing a flow of *E. coli* through the gold-microtube membrane, to the same system without flow is shown. The bacteria are resting on the membrane exposed to −4 V pulses.

Results show that using a flow-through experiment with a system as described herein can equate to about 20% of bacteria reversibly electroporated (FIG. 18A). This is 10-fold higher than the yield obtained with a commercial electroporator applying similar electric field gradients. The inhomogeneity of the electric field gradient distribution in a cuvette, associated with the difference in the length of the electric pulses, might explain this difference. The viability, however, may differ with a system as described herein as compared to the electroporator method (FIG. 18B). This can possibly be due to the flow, the length of the pulses, and/or the very high electric field gradients at the tube walls. Nevertheless, an 80% viability is considered in the acceptability range for electroporation, and systems and methods as described herein demonstrate suitable viability of cells for downstream applications.[18]

Without flow, a significant effect of electroporation may not be observed on the bacteria (FIGS. 18A-18B). This observation can be explained by the high number of bacteria in solution and the low porosity of the membrane. As such, most of the bacteria are far from the gold microtubes.

3. Conclusion

Described herein is a new electroporation device based on voltage charging[15, 16] of gold-microtube membranes in which cells are porated as they pass through the membrane. As shown herein, electric field gradients sufficient to porate *E. coli* can be achieved by applying small voltage pulses to the membrane. An optimal value of −4 V for electroporation of *E. coli* was predicted by simulation (FIG. 14A) and confirmed experimentally (FIG. 13). Furthermore, the percentage of reversibly electroporated bacteria was found to be more than an order of magnitude higher than obtained with a commercial electroporator, although the voltage employed was 500 times lower. Because the microtube membrane device is flow-through, higher throughput can be achieved compared to traditional batch-wise porators.

4. Experimental Section

Materials: Polycarbonate membrane filters from Poretics Corporation were used to prepare the gold-microtube membrane. Electroless gold-plating was carried using anhydrous $SnCl_2$, $Na_2SO_3$, $NaHCO_3$, and $AgNO_3$ from Sigma-Aldrich. Commercial gold solution (Oromerse Part B) was obtained from Technic, Inc. All other chemicals used for gold-plating were acquired through Fisher Scientific. NaCl, $KH_2PO_4$, $Na_2HPO_4$, KCl, Luria-Bertani (LB) broth (Lennox), and 1 mg $mL^{-1}$ propidium iodide (PI) solution in DMSO were obtained from Sigma-Aldrich. Glycerol (Thermo Scientific), absolute ethanol (Decon Labs.), 1 mM solution of YO-PRO-1 iodide in DMSO (Life Technologies) were used. All chemicals were of reagent grade and used as received. K-12 strain *Escherichia Coli* bacteria were obtained from Carolina. Purified water was obtained by passing house-distilled water through an Aries brand Gemini water filtration system.

Gold-Microtube Membranes: Gold-microtube membranes were prepared using an electroless plating method previously described.[16, 26] Polycarbonate membranes of 10 µm thickness, pore diameters ranging from 3 µm to 20 µm, and pore density from $2 \times 10^6$ to $4 \times 10^4$ $cm^{-2}$ respectively were used. These membranes were plated for 4 hours in a 4° C. water bath. One of the resulting gold surface films was abrasively removed using ethanol. Ohmic contact was made to the other gold surface film by attaching a strip of conductive copper tape (3M) (FIG. 11).

Preparation and Storage of Bacteria: LB Broth solution was prepared according to the manufacturer's instructions. The solution was sterilized at 200° C. for 10 min. It was then inoculated with *E. coli* bacteria and was cultured overnight at room temperature. The next day, a refrigerated Thermo centrifuge (CL3R) at 1-3° C. was used, and all materials and solutions were kept in ice. The cultured broth was centrifuged for 5 min at 5300 rpm and resuspended in ice-cold PBS buffer (137 mm NaCl, 2.7 mm KCl, 8.1 mm $Na_2HPO_4$, 1.5 mm $KH_2PO_4$, pH 7.5). The solution of bacteria was subsequently centrifuged 4 times in new PBS buffers and twice in 10% glycerol solutions in PBS. The bacteria in 10% glycerol were then aliquoted in tubes and stored at −80° C. for no more than six months. Bacteria Preparation for EP: Bacteria aliquots were thawed in ice. They were then centrifuged twice 3 min at 5500 rpm and were resuspended in ice-cold PBS buffer. YOPRO was added to the resulting bacteria solution at a concentration of 0.8 µm. The subsequent bacterial solution contained approximately $2 \times 10^8$ *E. coli* $mL^{-1}$.

Flow-Through Cell Set-Up: A 15 mm clear-jacketed 1.77 $cm^2$ Franz diffusion cell from PermeGear was used. A circulation of cold water in the cell's jacket was controlled with a Manostat pump. In the receiver chamber, 12 mL of a 0.8 µm YOPRO solution in PBS was added. A gold-microtube membrane was then placed between the feed and receiver chambers of the diffusion cell. Square-wave pulses were applied between the membrane and a platinum counter electrode using an EG&G Princeton Applied Research Potentiostat/Galvanostat Model 273.

Flow-Through EP: Three mL of the solution of bacteria and YOPRO were added to the upper feed chamber of the diffusion cell. Bacteria flowed from the feed chamber, through the membrane, into the receiver chamber at a flow rate of 2 µL s$^{-1}$ provided by a PumpPro MLP peristaltic pump. The solution was collected from a sealed capillary tube inserted in the receiver chamber sample port. It was analyzed continuously by an Agilent 8453 UV/VIS spectrophotometer. The optical density of the bacteria solution at 600 nm was recorded over time. After 40 min, the final absorbance was compared to the absorbance of the initial solution. The corresponding proportion of bacteria that had passed through the membrane was calculated.

Analysis of Bacteria by the Flow-Through Method: 600 µL samples of the solution exiting the lower chamber were collected every 5 min and transferred in a quartz cuvette. A Cary Eclipse Fluorescence Spectrophotometer was used to measure fluorescence intensities. Emissions of YOPRO were recorded at peak wavelengths of 509 nm after excitation at 491 nm. Later, propidium iodide (PI) was added at a concentration of 3 µm in each sample. After 30 min in the refrigerator, fluorescence emissions of PI were recorded at 618 nm after excitation at 540 nm. These measurements were used to calculate the percentages of viable and reversibly electroporated bacteria using the method described in Supporting Information.

Analysis of Bacteria by the Fluorescence-Microscopy Method: An Axioplan 2 Imaging fluorescence microscope and attached mercury lamp were used for taking fluorescence and bright-field micrographs. The bacteria were centrifuged before being plated on microscope slides. Images were recorded using an AxioCam microscope camera and AxioVision AC software. Around 100 images were collected randomly after each experiment. ImageJ software from NIH was used to determine the total bacteria count and the total number of green (YOPRO) and red (YOPRO and PI) fluorescent bacteria. A total of approximately 5000 bacteria were counted for each experiment. Averages and standard deviations of these measurements were established with respect to the proportions of reversibly and irreversibly electroporated bacteria for each image.

Commercial Electroporator. A BioRad *E. coli* Pulser was used. A bacteria aliquot was retrieved from storage and thawed on ice. It was then centrifuged 3 min and resuspended twice in Ultrapure water. YOPRO was added at a concentration of 0.8 µm. Afterward, 300 µL of bacteria solution were transferred to an EP cuvette with a 0.2 cm gap (BioRad) and electroporated at 2.5 kV. The solution was then diluted in 2.7 mL ice-cold PBS and left 30 min in ice. The absorbance and fluorescence intensity of YOPRO were measured before PI was added at a concentration of 3 µm. Then, PI fluorescence intensity was recorded.

Scanning Electron Microscopy: Electron micrographs were obtained using a Hitachi SU5000 Schottky Field-Emission Microscope. The gold-microtube membranes were imaged from the top surface, where the gold surface film had been removed. ImageJ software was used to obtain the thickness, the diameter and the density of the gold microtubes. The averages and standard deviations were determined from around 100 measurements in different images.

REFERENCES

[1] K. H. Schoenbach, F. E. Peterkin, R. W. Alden, S. J. Beebe, *IEEE Trans. Plasma Sci.* 1997, 25, 284; b) M. Kanduser, D. Miklavcic, in *Electrotechnologies for Extraction from Food Plants and Biomaterials* (Eds: E. Vorobiev, N. Lebovka), Kluwer Academic/Plenum Publ, New York, USA, 2008, pp. 1-37; c) J. C. Weaver, Y. A. Chizmadzhev, *Bioelectrochem. Bioenerg.* 1996, 41, 135.

[2] R. Stampfli, *An. Acad. Bras. Cienc.* 1958, 30, 57.

[3] T. Kotnik, W. Frey, M. Sack, S. H. Meglic, M. Peterka, D. Miklavcic, *Trends Biotechnol.* 2015, 33, 480.

[4] J. Gehl, *Acta Physiol. Scand.* 2003, 177, 437.

[5] D. Luo, W. M. Saltzman, *Nat. Biotechnol.* 2000, 18, 33.

[6] P. A. Garcia, Z. F. Ge, J. L. Moran, C. R. Buie, *Sci. Rep.* 2016, 6, 11.

[7] S. Movahed, D. Q. Li, *Microfluid. Nanofluid.* 2011, 10, 703.

[8] a) W. G. Lee, U. Demirci, A. Khademhosseini, *Integr. Biol.* 2009, 1, 242; b) T. Geng, C. Lu, *Lab Chip* 2013, 13, 3803.

[9] J. Olofsson, K. Nolkrantz, F. Ryttsen, B. A. Lambie, S. G. Weber, O. Orwar, *Curr. Opin. Biotechnol.* 2003, 14, 29.

[10] A. Adamo, A. Arione, A. Sharei, K. F. Jensen, *Anal. Chem.* 2013, 85, 1637; b) D. Y. Zhao, D. Huang, Y. Li, M. X. Wu, W. F. Zhong, Q. Cheng, X. X. Wang, Y. D. Wu, X. Zhou, Z. W. Wei, Z. H. Li, Z. C. Liang, *Sci. Rep.* 2016, 6, 9; c) S. O. Choi, Y. C. Kim, J. W. Lee, J. H. Park, M. R. Prausnitz, M. G. Allen, Small 2012, 8, 1081; d) S. H. Kim, T. Yamamoto, D. Fourmy, T. Fujii, Small 2011, 7, 3239.

[11] T. Geng, Y. H. Zhan, J. Wang, C. Lu, *Nat. Protoc.* 2011, 6, 1192; b) P. E. Boukany, A. Morss, W. C. Liao, B. Henslee, H. C. Jung, X. L. Zhang, B. Yu, X. M. Wang, Y. Wu, L. Li, K. L. Gao, X. Hu, X. Zhao, O. Hemminger, W. Lu, G. P. Lafyatis, L. J. Lee, *Nat. Nanotechnol.* 2011, 6, 747; c) K. L. Gao, L. Li, L. N. He, K. Hinkle, Y. Wu, J. Y. Ma, L. Q. Chang, X. Zhao, D. G. Perez, S. Eckardt, J. McLaughlin, B. Y. Liu, D. F. Farson, L. J. Lee, Small 2014, 10, 1015.

[12] L. Q. Chang, M. Howdyshell, W. C. Liao, C. L. Chiang, D. Gallego-Perez, Z. G. Yang, W. Lu, J. C. Byrd, N. Muthusamy, L. J. Lee, R. Sooryakumar, Small 2015, 11, 1818; b) Z. Z. Fei, X. Hu, H. W. Choi, S. N. Wang, D. Farson, L. J. Lee, *Anal. Chem.* 2010, 82, 353; c) X. Xie, A. M. Xu, S. Leal-Ortiz, Y. H. Cao, C. C. Garner, N. A. Melosh, *ACS Nano* 2013, 7, 4351.

[13] M. B. Fox, D. C. Esveld, A. Valero, R. Luttge, H. C. Mastwijk, P. V. Bartels, A. van den Berg, R. M. Boom, *Anal. Bioanal. Chem.* 2006, 385, 474.

[14] S. N. Wang, L. J. Lee, *Biomicrofluidics* 2013, 7, 14.

[15] M. Nishizawa, V. P. Menon, C. R. Martin, *Science* 1995, 268, 700; b) S. B. Lee, C. R. Martin, *J. Am. Chem. Soc.* 2002, 124, 11850; c) M. S. Kang, C. R. Martin, *Langmuir* 2001, 17, 2753.

[16] P. Gao, C. R. Martin, *ACS Nano* 2014, 8, 8266.

[17] C. R. Martin, *Science* 1994, 266, 1961.

[18] V. P. Menon, C. R. Martin, *Anal. Chem.* 1995, 67, 1920.

[19] W. J. Dower, J. F. Miller, C. W. Ragsdale, *Nucleic Acids Res.* 1988, 16, 6127; b) P. J. Canatella, P. J. Karr, J. A. Petros, M. R. Prausnitz, *Biophys. J.* 2001, 80, 755.

[20] G. Sezonov, D. Joseleau-Petit, R. D'Ari, *J. Bacteriol.* 2007, 189, 8746; b) J. A. Myers, B. S. Curtis, W. R. Curtis, *BMC Biophys.* 2013, 6, 15.

[21] A. G. Pakhomov, E. Gianulis, P. T. Vernier, I. Semenov, S. Xiao, O. N. Pakhomova, *Biochim. Biophys. Acta, Biomembr.* 2015, 1848, 958.

[22] P. T. Vernier, Y. H. Sun, M. A. Gundersen, *BMC Cell Biol.* 2006, 7, 16.

[23] T. L. Netzel, K. Nafisi, M. Zhao, J. R. Lenhard, I. Johnson, *J. Phys. Chem.* 1995, 99, 17936.

[24] J. D. Deng, K. H. Schoenbach, E. S. Buescher, P. S. Hair, P. M. Fox, S. J. Beebe, *Biophys. J.* 2003, 84, 2709.

[25] A. J. Bard, L. R. Faulkner, *Electrochemical Methods: Fundamentals and Applications, 2nd ed.,* John Wiley & Sons, New York, 2001; b) Z. J. Jiang, D. Stein, *Phys. Rev. E* 2011, 83, 6; c) H. S. White, A. Bund, *Langmuir* 2008, 24, 2212.

[26] S. Fujii, S. Honda, H. Machida, H. Kawai, K. Ishida, M. Katayama, H. Furuta, T. Hirao, K. Oura, *Appl. Phys. Lett.* 2007, 90, 3.

[27] L. Rizzello, B. Sorce, S. Sabella, G. Vecchio, A. Galeone, V. Brunetti, R. Cingolani, P. P. Pompa, *ACS Nano* 2011, 5, 1865.

[28] C. R. Martin, M. Nishizawa, K. Jirage, M. Kang, *J. Phys. Chem. B* 2001, 105, 1925.

Supplemental Information

FIG. 23 shows embodiments of pore diameters and densities of nucleopore polycarbonate microporous membranes.

FIGS. 24A-24D. show fluorescence excitation and emission spectra of a) YOPRO 0.8 µM in PBS, b) YOPRO 0.8 µM in a solution of $4\times10^7$ *E. coli* $mL^{-1}$ in PBS, c) PI 3 µm in PBS, and d) PI 3 µm in a solution of $4\times10^7$ *E. coli* $mL^{-1}$ in PBS. The bacteria have been lysed with ethanol prior to the fluorescence intensity measurements.

FIGS. 25A-25D. Micrographs of the top face of the gold-microtube membranes after electroporation experiments with different voltage pulses. The green fluorescence results from YOPRO in electroporated bacteria. The gold tubes are seen in white. In each case, bright-field and fluorescence images are overlaid.

FIGS. 26A-26D. Micrographs of the top face of the gold-microtube membranes after electroporation experiments with different tube diameters. The green fluorescence results from YOPRO in electroporated bacteria. The gold tubes are seen in white. In each case, bright-field and fluorescence images are overlaid.

Example 3

Introduction

Cell permeation relies on an efficient method to allow the uptake of exogenous molecules through the cell membrane. In this regard, the use of a short electric pulse has proven to create temporary pores in their membrane that can allow the introduction of exogenous molecules into a cell. However this approach suffers from the need of high voltage, up to 2 kV, leading to cell lysis and limited control over the amount of cells electroporated. The present example focuses on the design and characterization of a microporous gold-plated polycarbonate membrane for flow-through electroporation at low voltages. As *Escherichia coli* pass through the membrane, they can experience a high electric field that allows a DNA staining dye, YOPRO-1 iodide, in solution to penetrate the bacterial cell wall/membrane and be detected by fluorescence spectroscopy and microscopy. Another membrane-impermeable dye, propidium iodide, is then added to the solution in order to determine the viability.

Voltage Pulses

Figure 19:
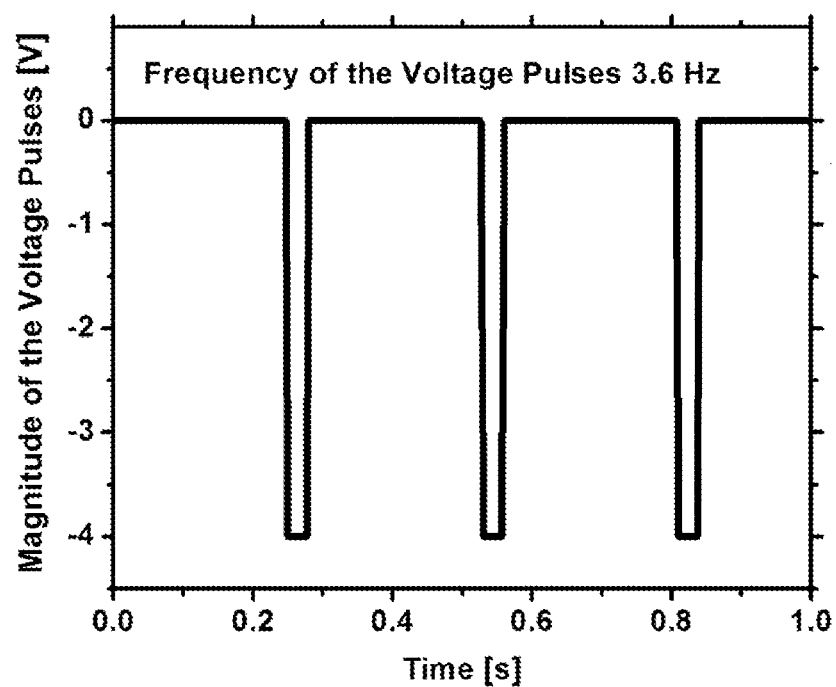
FIG. 19 shows an embodiment of a pulse sequence applied to the membrane.
Figures 20A, 20B, 20C, 20D, 20E, 20F:
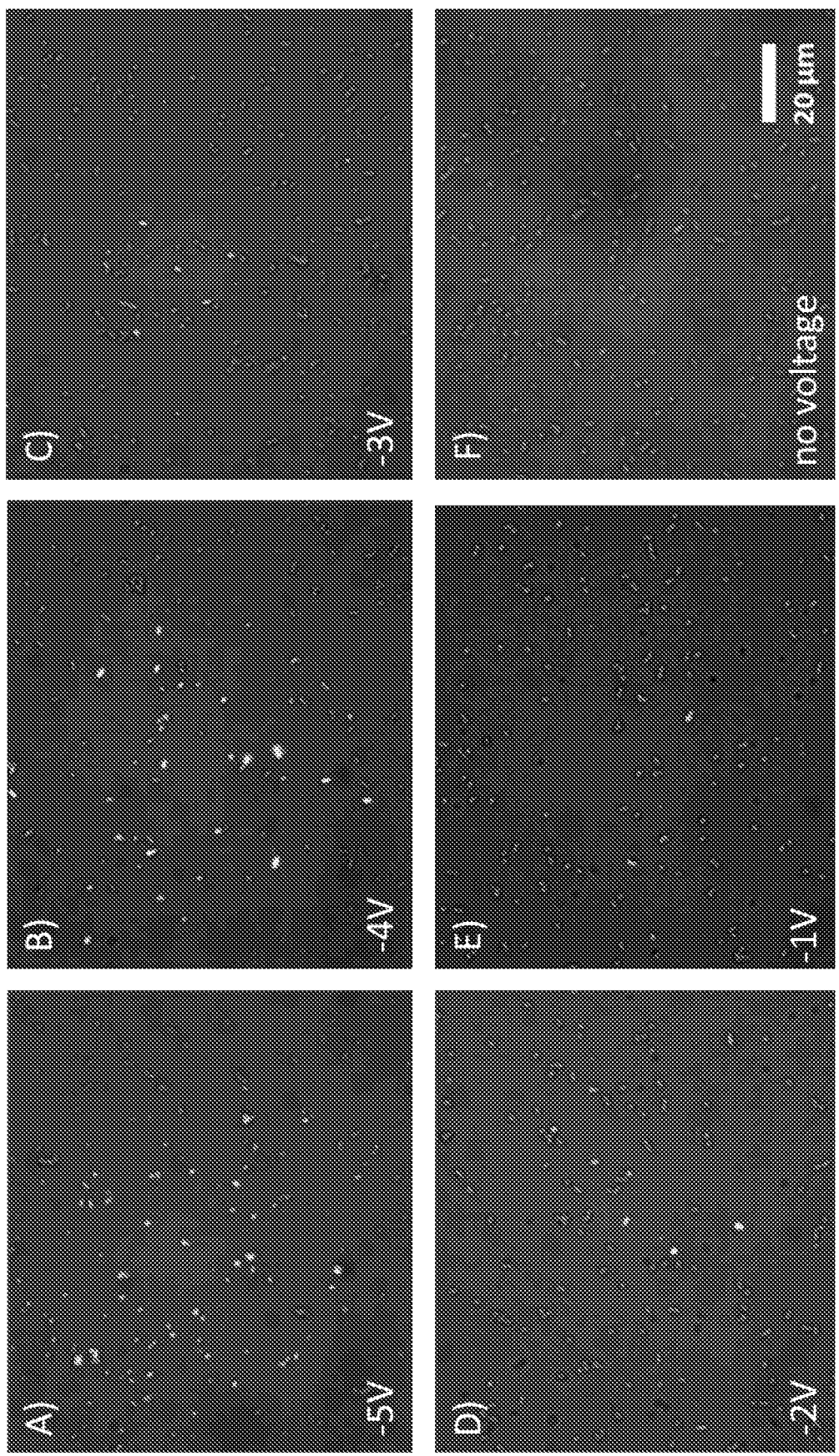
FIGS. 20A-20F are pictures of fluorescence-emitting bacteria after electroporation at different voltages. −5V, −4V, −3V, −2V, −1V, and no voltage were used in FIGS. 20A-20F respectively.
Figure 21:
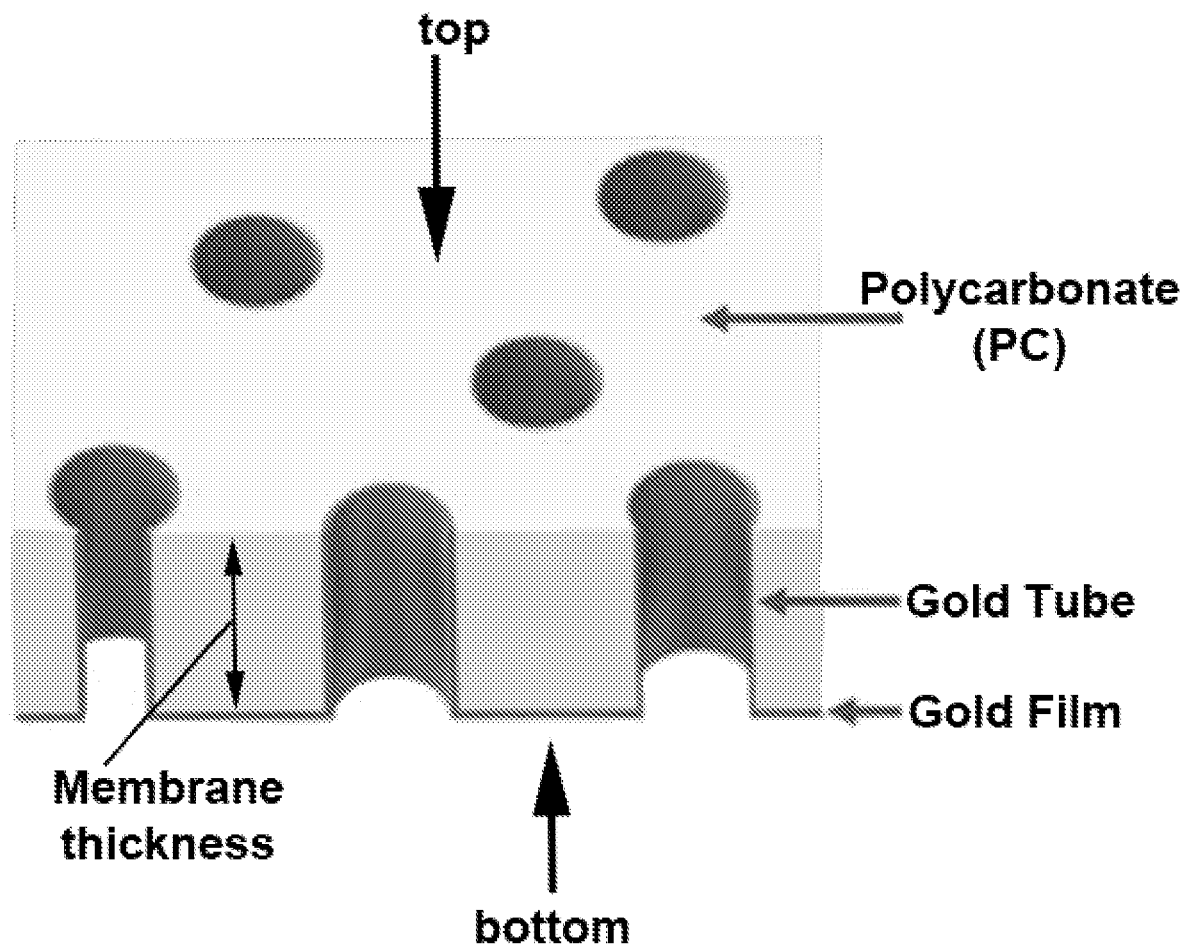
FIG. 21 is an illustration of a representative section of an embodiment of a conductive porous membrane according to the present disclosure showing various features.
Figure 22:
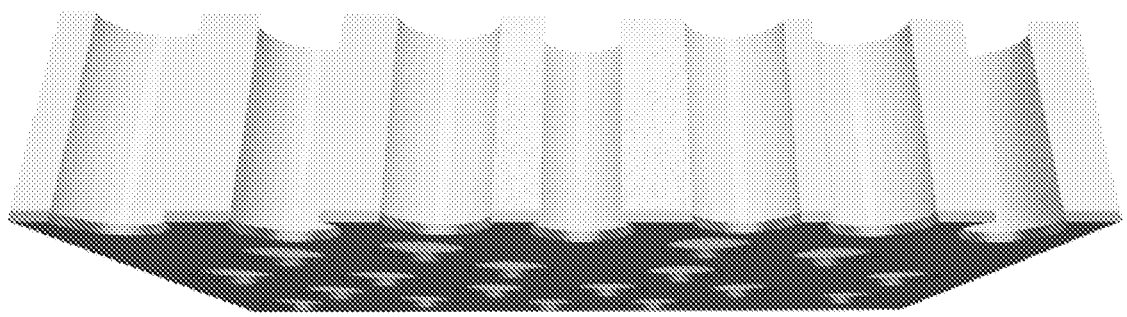
FIG. 22 is an illustration of a representative section of an embodiment of a porous membrane with a coating on one surface according to the present disclosure.
Figure 24A:
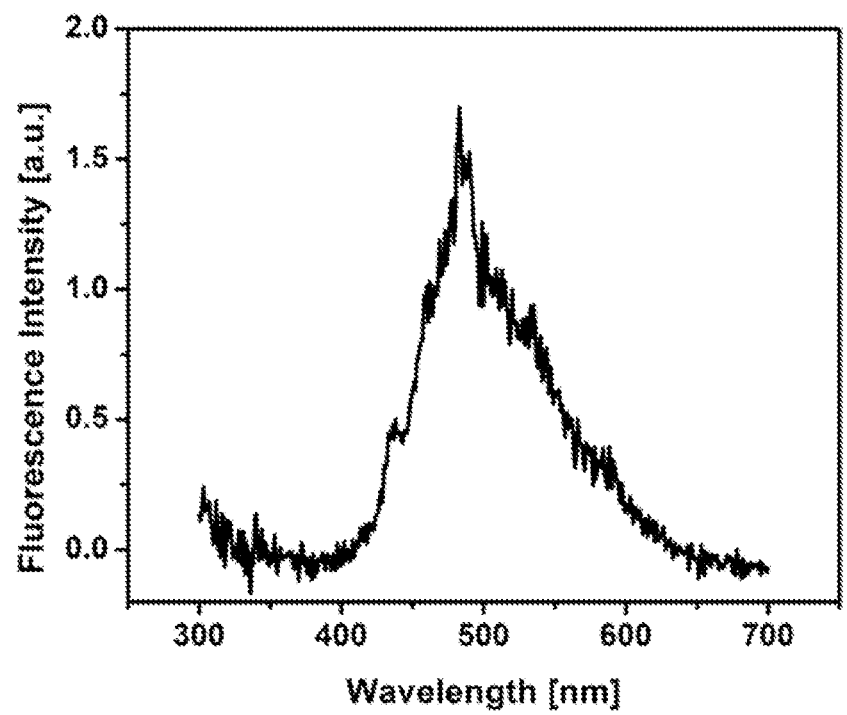
FIG. 24A depicts fluorescence excitation and emission spectra of 0.8 µM YOPRO in PBS.
Figure 24B:
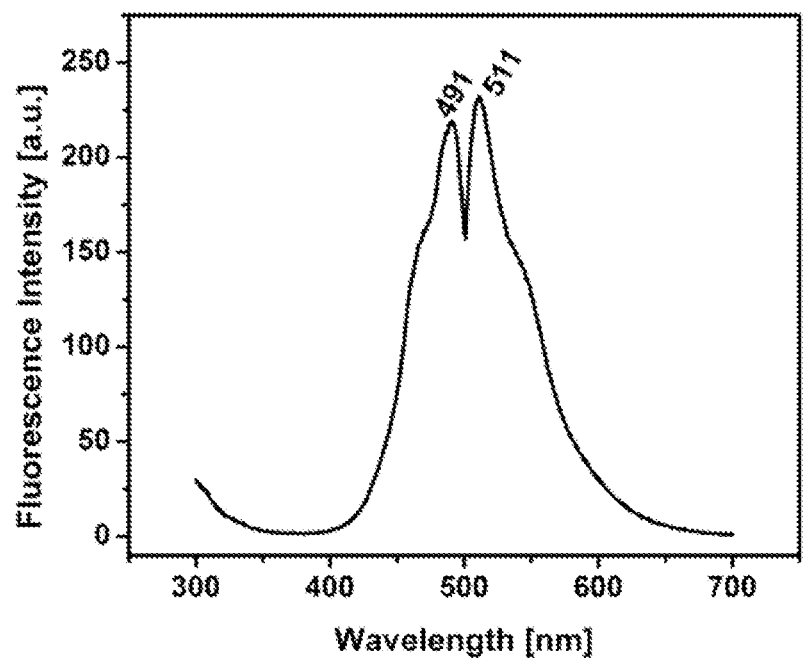
FIG. 24B shows 0.8 µM YOPRO in a solution of $4 \times 10^7$ lysed $E.$ $coli$ $mL^{-1}$ in PBS.
Figure 24C:
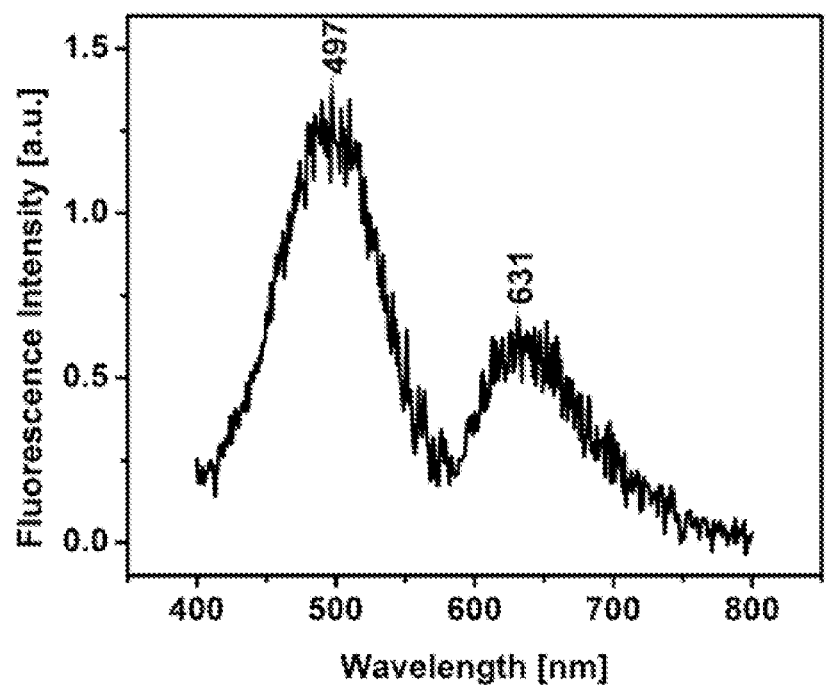
FIG. 24C shows 3 µM PI in PBS.
Figure 24D:
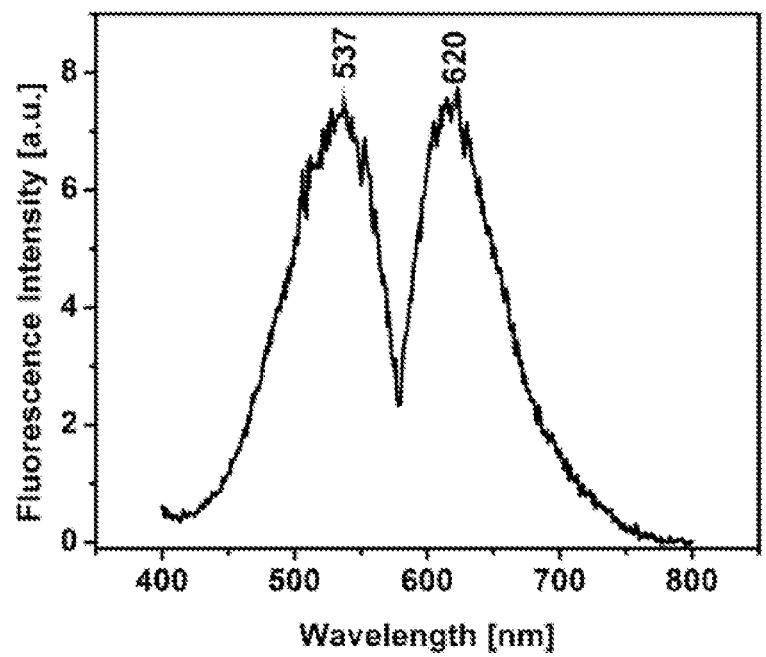
FIG. 24D shows 3 µM PI in a solution of $4 \times 10^7$ lysed $E.$ $coli$ $mL^{-1}$ in PBS.
Figures 25A, 25B, 25C, 25D, 25E, 25F:
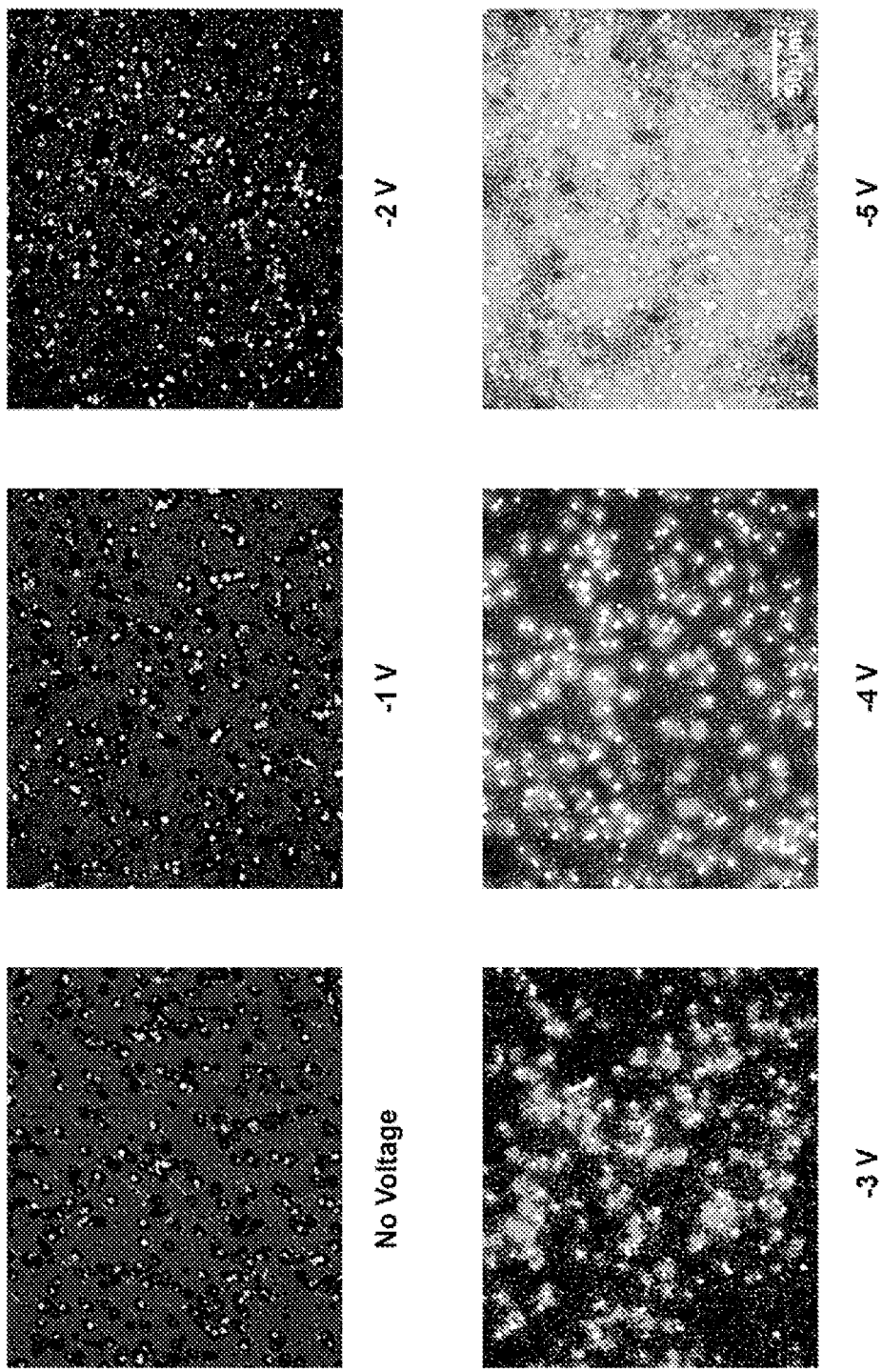
FIGS. 25A-25F show micrographs of a face of the gold-microtube membranes after electroporation experiments with different magnitude of the voltage pulses. The green fluorescence results from YOPRO in electroporated bacteria. The gold tubes are seen in white. In each case, brightfield and fluorescence images are overlaid.
Figures 26A, 26B, 26C, 26D:
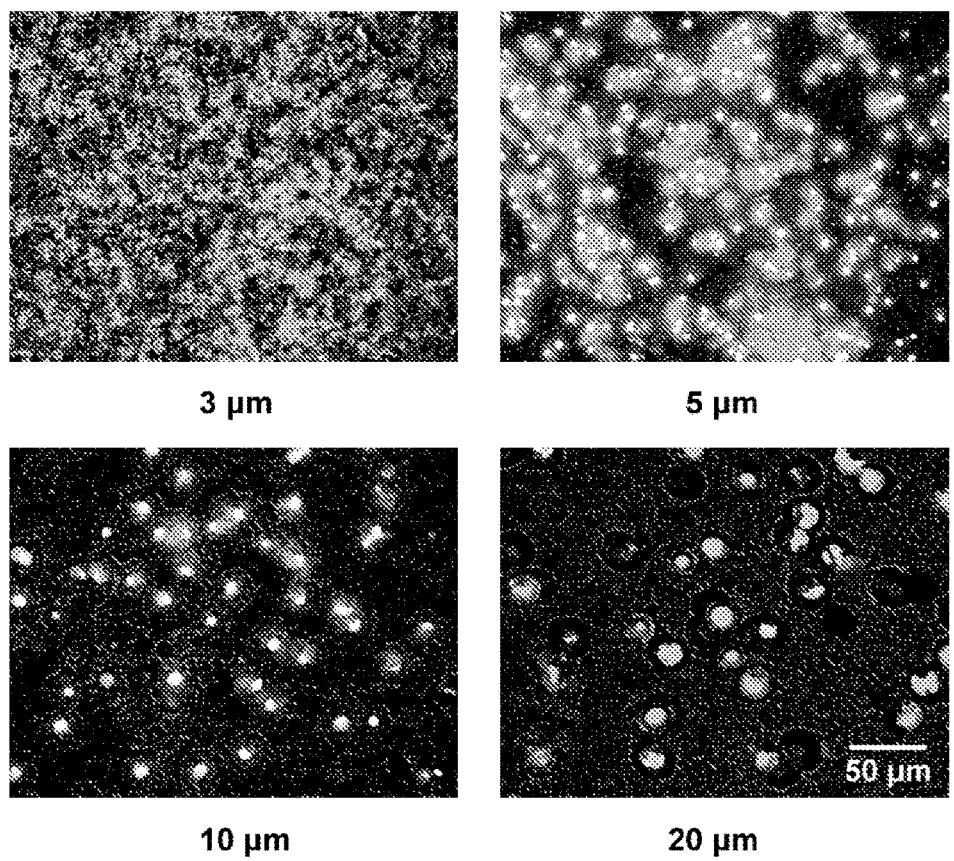
FIGS. 26A-26D depict micrographs of the top face of the gold-microtube membranes after electroporation experiments with different average tube diameters. The green fluorescence results from YOPRO in electroporated bacteria. The gold tubes are seen in white. In each case, brightfield and fluorescence images are overlaid.

FIG. 19 shows a representative pulse sequence for flow-through electroporation according to the present disclosure. 30 ms pulses at −4 V every 250 ms are applied to the membrane during electroporation. Pulses can be applied to the side of the membrane that is coated only. About 5,000 pulses are applied during an electroporation experiment. Microscope pictures of the fluorescent bacteria after electroporation from no voltage to −4V are shown in FIGS. 20A-20F. FIGS. 21, 22, and 27 show embodiments of porous membranes as used herein. The side with the gold plating (designated the "bottom" in FIG. 21 can face a feed chamber or a receiver chamber. Fluorescent bacteria can correspond to successfully reversibly electroporated bacteria according to systems and methods of the present disclosure. As shown in FIGS. 21 and 27, a side of the membrane can lack a coating of conductive material, and this side can be the top of a membrane (shown in FIG. 21). FIG. 22 represents an embodiment of a porous membrane wherein the pores (aka tubes) lack a coating of conductive material on the inside surface[s] of the pores.

Conclusions

It has recently been established that it can be possible to use an alternate geometry for electroporation to allow for safe and efficient electroporation with a lower energy cost compared to conventional systems and methodology. The use of a microporous gold membrane can result in a large percentage of *E. coli* electroporated using a voltage as low as +/−4 V. The continuous-flow model presented and described herein can produce high volumes of treated cells, from µL to mL, in a few minutes. Variables such as membrane pore size, membrane pore density, flow rate, voltage, and various cell preparations can be altered and optimized according to the equations, methods, and systems herein according to the desired cell type to undergo electroporation Unless defined otherwise, all technical and scientific terms used have the same meaning as commonly understood by one of ordinary skill in the art to which this disclosure belongs. Although any methods and materials similar or equivalent to those described can also be used in the practice or testing of the present disclosure, the preferred methods and materials are now described.

Embodiments of the present disclosure will employ, unless otherwise indicated, techniques of separating, testing, and constructing materials, which are within the skill of the art. Such techniques are explained fully in the literature.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

The invention claimed is:

1. A flow-through electroporation system comprising:
   a chamber with a first and a second portion,
      wherein the first portion is configured to receive cells,
      wherein the second portion is in fluid communication with the first portion and is configured to receive cells from the first portion,
      wherein an electrode is present in the first portion or both the first portion and the second portion;
   a porous membrane separating the first and second portions, the membrane having one or more pores and coated with a conductive material on one or more sides,
      wherein the electrode is not in physical contact with the membrane inside the first portion;
      wherein the one or more pores have one or more interior surfaces coated with gold microtubes and are configured to allow cells from the first portion to pass through to the second portion; and
   an electric generating device in electrical communication with one or more electrodes, the membrane, or the one or more electrodes and the membrane, wherein the electric generating device is configured to deliver constant voltage or one or more electric pulses to the system.

2. The flow-through electroporation system of claim 1, wherein the porous membrane has a thickness of about 100 nm to 10 cm.

3. The flow-through electroporation system of claim 1, wherein the one or more pores have an average diameter of about 10 nm to about 5 mm.

4. The flow-through electroporation system of claim 1, wherein the one or more pores have a length of about 100 nm to about 10 cm.

5. The flow-through electroporation system of claim 1, wherein the one or more electric pulses comprise a −4V volt DC pulse with a 30 ms duration and a period of 250 ms.

6. The flow-through electroporation system of claim 1, wherein the one or more pores are coated with a conductive material on one or more interior surfaces.

7. The flow-through electroporation system of claim 6, wherein the conductive material is a metal selected from the group consisting of gold, silver, platinum, nickel, aluminum, tin, copper, molybdenum, zinc, tungsten, carbon, iron, palladium, titanium, lead, mercury, lithium, brass, metal oxides, manganese, magnesium and combinations thereof.

8. The flow-through electroporation system of claim 1, wherein the porous membrane comprises gold, silver, platinum, nickel, aluminum, tin, copper, molybdenum, zinc, tungsten, carbon, iron, palladium, titanium, lead, mercury, lithium, brass, manganese, magnesium, metal oxides or combinations thereof.

9. The flow-through electroporation system of claim 1, wherein the porous membrane further comprises polycarbonate, polyethylene terephthalate, myca, aluminum, aluminum oxide, nylon, polytetrafluoroethylene, silicon, cellulose, polypropylene, polyvinylidene fluoride, silver, polyethersulfone, or combinations thereof.

10. The flow-through electroporation system of claim 1, wherein the second portion further comprises a stirring device.

11. A flow-through electroporation system comprising:
a chamber with a first and a second portion,
   wherein the first portion is configured to receive cells,
   wherein the second portion is in fluid communication with the first portion and is configured to receive cells from the first portion,
   wherein an electrode is present in the second portion;
a porous membrane separating the first and second portions, the membrane having one or more pores with a pore density of about 1 pore/m$^2$ to about $10^{15}$ pores/cm$^2$ and the membrane coated with a conductive material on one or more sides,
   wherein the one or more pores have one or more interior surfaces coated with gold microtubes and are configured to allow cells from the first portion to pass through to the second portion; and
an electric generating device in electrical communication with one or more electrodes, the membrane, or the one or more electrodes and the membrane, wherein the electric generating device is configured to deliver constant voltage or one or more electric pulses to the system; and
a cooling device to lower the temperature of the second portion.

12. The flow-through electroporation system of claim 11, wherein the porous membrane has a thickness of about 100 nm to 10 cm.

13. The flow-through electroporation system of claim 11, wherein the one or more pores have an average diameter of about 10 nm to about 5 mm.

14. The flow-through electroporation system of claim 11, wherein the one or more pores have a length of about 100 nm to about 10 cm.

15. The flow-through electroporation system of claim 11, wherein the one or more pores are coated with a conductive material on one or more interior surfaces.

16. The flow-through electroporation system of claim 15, wherein the conductive material is a metal selected from the group consisting of gold, silver, platinum, nickel, aluminum, tin, copper, molybdenum, zinc, tungsten, carbon, iron, palladium, titanium, lead, mercury, lithium, brass, manganese, magnesium, metal oxides and combinations thereof.

17. The flow-through electroporation system of claim 11, wherein the porous membrane comprises gold, silver, platinum, nickel, aluminum, tin, copper, molybdenum, zinc, tungsten, carbon, iron, palladium, titanium, lead, mercury, lithium, brass, metal oxides and combinations thereof.

18. The flow-through electroporation system of any of claim 11, wherein the porous membrane further comprises polycarbonate, polyethylene terephthalate, myca, aluminum, aluminum oxide, nylon, polytetrafluoroethylene, silicon, cellulose, polypropylene, polyvinylidene fluoride, silver, polyethersulfone, or combinations thereof.

19. The flow-through electroporation system of claim 11, wherein the second portion further comprises a stirring device.

* * * * *